(12) United States Patent
Oda et al.

(10) Patent No.: US 8,131,479 B2
(45) Date of Patent: Mar. 6, 2012

(54) METHOD OF PROTEOME ANALYSIS FOR PHOSPHORYLATED PROTEIN

(75) Inventors: Yoshiya Oda, Tsukuba (JP); Tsuyoshi Tabata, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 630 days.

(21) Appl. No.: 11/630,927

(22) PCT Filed: Jul. 4, 2005

(86) PCT No.: PCT/JP2005/012714
§ 371 (c)(1), (2), (4) Date: Dec. 27, 2006

(87) PCT Pub. No.: WO2006/004214
PCT Pub. Date: Jan. 12, 2006

(65) Prior Publication Data
US 2008/0221802 A1 Sep. 11, 2008

(30) Foreign Application Priority Data
Jul. 2, 2004 (JP) ................................ 2004-197344

(51) Int. Cl.
*G06F 19/00* (2006.01)
*G01R 23/02* (2006.01)
(52) U.S. Cl. .......................................... 702/19; 250/282
(58) Field of Classification Search ........................ None
See application file for complete search history.

(56) References Cited

FOREIGN PATENT DOCUMENTS

| | | |
|---|---|---|
| EP | 1477800 A1 | 11/2004 |
| JP | 2003-521257 A | 7/2003 |
| WO | WO-01/57519 A2 | 8/2001 |
| WO | WO-02/072863 A2 | 9/2002 |
| WO | WO-03/058206 A1 | 7/2003 |
| WO | WO-03/06503 A1 | 8/2003 |

OTHER PUBLICATIONS

Neville et al. Evidence for phosphorylation of serine 753 in CFTR using a novel metal-ion affinity resin and matrix-assisted laser desorption mass spectrometry Protein Science vol. 6, pp. 2436-2445 (1997).*
Gygi et al. Protein analysis by mass spectrometry and sequence database searching: Tools for cancer research in the post-genomic era Electrophoresis vol. 20, pp. 310-319 (1999).*
Ficarro et al. Phosphoproteome analysis by mass spectrometry and its application to *Saccharomyces cerevisiae* Nature Biotechnology vol. 20, pp. 301-305 (2002).*
Zhou, Huilin et al.; "A systematic approach to the analysis of protein phosphorylation"; Nature Biotechnology, Nature Publishing Group, New York, NY, vol. 19, Apr. 2001, pp. 375-378.
Aebersold, Ruedi et al.; "Mass Spectrometry in Proteomics"; Chemical Reviews, 2001, vol. 101, No. 2, pp. 269-295.

Yoshiya Oda, "phospation Proteome Kaiseki no Saishin Gijutsu", Experimental Medicine, vol. 20, No. 1., pp. 23 to 27, Jan. 1, 2002.
Yoshiya Oda, "Tanpakushitsu no Hon'yakugo Shushoku no Kaiseki", Gendai Kagaku, Zokan 42 Proteomics-Hoho to sono Byotai Kaiseki eno Oyo-, pp. 24 to 30, Oct. 10, 2002.
Hisashi Hirano, et al., "Tanpakushitsu no Hon'yakugo Shushoku no Kaiseki", Experimental Medicine, vol. 20, No. 14, pp. 45 to 50, Sep. 25, 2002.
Notice of Reasons for Rejection for corresponding Japanese Patent Appl No. 2006-529017, mail date Apr. 13, 2010 (Japanese language and English translation attached).
Posewitz, Matthew C. et al.; "Immobilized Gallium(III) Affinity Chromatography of Phosphopeptides"; Analytical Chemistry, vol. 71, No. 14, Jul. 15, 1999, pp. 2883-2892.
Nuehse, Thomas S. et al.; "Large-scale Analysis of in Vivo Phosphorylated Membrane Proteins by Immobilized Metal Ion Affinity Chromatography and Mass Spectrometry"; Molecular & Cellular Proteomics, The American Society for Biochemistry and Molecular Biology, Inc., vol. 2, No. 11, Nov. 2003, pp. 1234-1243.
Haydon, Claire E. et al.; "Identification of Novel Phosphorylation Sites on *Xenopus laevis* Aurora A and Analysis of Phosphopeptide Enrichment by Immobilzed Metal-affinity Chromatography"; Molecular & Cellular Proteomics, The American Society for Biochemistry and Molecular Biology, Inc., vol. 2, No. 10, Oct. 2003, pp. 1055-1067.
Hirschberg, Daniel et al.; "Detection of Phosphorylated Peptides in Proteomic Analyses Using Microfluidic Compact Disk Technology"; Analytical Chemistry, vol. 76, No. 19, Oct. 1, 2004, pp. 5864-5871.
European Search Report issued for corresponding EP Application No. 09 00 9136, dated Oct. 1, 2009.
Shou, Wenying et al.: "Mapping Phosphorylation Sites in Proteins by Mass Spectrometry"; Methods in Enzymology, vol. 351, pp. 279-296. (2002).
McLachlin, Derek T. et al.; "Analysis of phosphorylated proteins and peptides by mass spectrometry"; Curr Opin Chem Biol., 2001, vol. 5; pp. 591.602.
Drewes, Gerard et al.; "Global approaches to protein-protein interactions"; Current Opinion in Cell Biology 2003, vol. 15, pp. 199-205.
Watts, Julian D. et al.; "Identification by Electrospray Ionization Mass Spectrometry of the Sites of Tyrosine Phosphorylation Induced in Activated Jurkat T Cells on the Protein Tyrosine Kinase Zap-70*"; The Journal of Biological Chemistry, vol. 269, No. 47, Issue of Nov. 25, 1994, pp. 29520-29529.
Michel, Hanspeter et al.; "Tandem Mass Spectrometry Identifies Sites of Three Post-translational Modifications of Spinach Light-harvesting Chlorophyll Protein II"; The Journal of Biological Chemistry, vol. 266, No. 26, Issue of Sep. 15, 1991, pp. 17584-17591.

(Continued)

*Primary Examiner* — John S Brusca
(74) *Attorney, Agent, or Firm* — Dickstein Shapiro LLP

(57) ABSTRACT

A method for detecting plural types of phosphorylated proteins in a sample, wherein a database consisting of data regarding plural types of proteins in the sample is used; and a method for purifying phosphorylated proteins using an immobilized metal carrier or a titania carrier, wherein a solution containing acetonitrile in a range of 40% (v/v) or greater but 60% (v/v) or less is used.

3 Claims, 4 Drawing Sheets

OTHER PUBLICATIONS

Neville, David C.A. et al.; Evidence for phosphorylation of serine 753 in CFTR using a novel metal-ion affinity resin and matrix-assisted laser desorption mass spectrometry; Protein Science, 1997, vol. 6, pp. 2436-2445.

Wu, Xiaohua, et al.; "ATM phosphorylation of Nijmegen breakage syndrome protein is required in a DNA damage response"; Nature, vol. 405, May 25, 2000, pp. 477-482.

Stensballe, A. et al.; "Characterization of phosphoproteins from electrophoretic gels by nanoscale Fe(III) affinity chromatography with off-line mass spectrometry analysis"; Proteomics 2001, vol. 1, pp. 207-222.

Zhou, Wei, et a.; "Detection and Sequencing of Phosphopeptides Affinity Bound to Immobilized Metal Ion Beads by Matrix-Assisted Laser Desorption/Ionization Mass Spectrometry"; J Am Soc Mass Spectrum 2000, vol. 11, pp. 273-282.

Nuwaysir, Lydia M. et al.; "Electrospray Ionization Mass Spectrometry of Phosphopeptides Isolated by On-Line Immobilized Metal-Ion Affinity Chromatography"; J Am Soc Mass Spectrum 1993, vol. 3, pp. 662-669.

* cited by examiner

FIG. 2

<Example: in the case of NCBInr database>

>gi|2853677|gb|AAC02458.1| T cell receptor delta chain [Homo sapiens]

ERDEGSYYCACDTVLGDTPSSWDT

>gi|2564245|emb|CAA73606.1| protein X [Homo sapiens]

MAASWRLGCDPRLLRYLVGFPGRRSVGLVKGALGWSVSRGANWRWFH
STQWLRGDPIKILMPSLSPTMEEGNIVKWLKKEGEAVSAGDALCEIETD
KAVVTLDASDDGILAKIVVEEGSKNIRLGSLIGLIVEEGEDWKHVEIPKD
VGPPPPVSKPSEPRPSPEPQISIPVKKEHIPGTLRFRLSPAARNILEKHSL
DASQGTATGPRGIFTKEDALKLVQLKQTGKITESRPTPAPTATPTAPSPL
QATSGPSYPRPVIPPVSTPGQPNAVGTFTEIPASNIRRVIAKRLTESKSTV
PHAYATADCDLGAVLKVRQDLVKDDIKVSVNDFIIKAAAVTLKQMPDVN
VSWDGEGPKQLPFIDISVAVATDKGLLTPIIKDAAAKGIQEIADSVKALSK
KARDGKLLPEEYQGGSFSISNLGMFGIDEFTAVINPPQACILAVGRFRPV
LKLTEDEEGNAKLQQRQLITVTMSSDSRVVDDELATRFLKSFKANLEN
PIRLA

METHOD OF PROTEOME ANALYSIS FOR PHOSPHORYLATED PROTEIN

TECHNICAL FIELD

The present invention relates to a method for detecting plural types of phosphorylated proteins in a sample, wherein a database consisting of data regarding plural types of proteins in the sample is used. The present invention also relates to a method for purifying (herein, the term "purification" encompasses separation and/or enrichment) one or plural types of phosphorylated proteins in a sample using an immobilized metal carrier or a titania carrier, wherein a solution containing acetonitrile in a range of 40% (v/v) (representing the volume to volume percentage; this is applied both in the specification and the claims) or greater but 60% (v/v) or less is used.

BACKGROUND ART

It is known that many proteins are modified in various manners after being translated. Among the modifications, phosphorylation of proteins is important as a factor for changing various physiological activities and enzymatic activities of proteins to regulate intracellular signal transduction or intracellular metabolic activities. Therefore, it is very important to analyze intracellular phosphorylation of proteins. Conventionally, various techniques have been developed for examining phosphorylation of proteins, one of which uses mass spectrometry[1].

Mass spectrometry is practically performed as follows. Proteins separated and purified by electrophoresis or the like are treated with enzymatic digestion, and measured by MALDI-TOF/MS or the like. The resultant peptide-mass fingerprint is checked against a database to identify proteins. When there is a peptide chain which is larger by 80 Da than the theoretical value obtained from the primary amino acid sequence, there is a high possibility that one site of the peptide chain is phosphorylated. Then, the peptide chain is treated with alkaline phosphatase to specifically remove the phosphoric acid group from the peptide chain, and the peptide chain is again measured by mass spectrometry. When the peptide chain is now smaller by 80 Da and matches the theoretical value, it is proved that the peptide chain was phosphorylated at one site[2].

Regarding phosphorylation of one protein, it is possible to identify the phosphorylated peptide and the phosphorylated site by digesting the proteins and analyzing peptide fractions using a mass spectrometer.

In proteome analysis, however, several hundred to several thousand proteins are measured at once. The term "proteome analysis" refers to an analysis of clarifying the relationship between the gene information and various types of proteins interacting in a cell in a complicated manner[3]. Namely, proteome analysis refers to a technique of comprehensively analyzing all the proteins included in the cell.

For this reason, in proteome analysis, it is extremely difficult to check mass spectra one by one. In most cases, the result provided by an automatic search engine (e.g., MASCOT) is accepted as being correct with no checking.

Usually, proteome analysis uses a protein database (e.g., NCBInr, IPI, or Sport). When an automatic search engine (e.g., MASCOT) is used, a great number of pseudopositive and pseudonegative results are provided and the search requires a huge amount of time. For these reasons, it is difficult to perform proteome analysis with high efficiency and high precision.

Usually, most proteins contain phosphorylated molecules and non-phosphorylated molecules in a mixed state. There is almost no protein in which most protein molecules are phosphorylated. One protein molecule is occasionally phosphorylated at a plurality of sites, or is mixed with other types of proteins. Therefore, it is difficult to directly detect a phosphorylated protein by mass spectrometry.

In addition, it is generally known that when a protein is phosphorylated, the detection sensitivity for the protein by a mass spectrometry is decreased. Therefore, when the intended proteins are not purified to a high degree or are only purified in a small amount, it is difficult to detect phosphorylated proteins. When the amount of proteins in a sample is extremely small, it is very difficult to detect phosphorylated proteins. In order to comprehensively analyze phosphorylated proteins, it is desirable to first specifically purify and then measure the phosphorylated proteins with a mass spectrometer.

One generally used method for specifically purifying phosphorylated proteins is immobilized metal affinity chromatography (hereinafter, occasionally referred to as "IMAC"). An IMAC column is formed of metal such as tertiary iron ions or gallium immobilized on a chelate forming group with a plurality of carboxylic acids. Since a phosphoric acid group specifically and strongly binds to tertiary iron ions, a phosphorylated protein can be bound to the IMAC column. For binding a phosphoric acid group to the IMAC column, acid conditions are used. For releasing the phosphoric acid group, the pH value of the solvent is made weakly alkaline or competitive elution means using a phosphoric acid buffer solution is used[4-12].

However, it is not easy to purify only phosphorylated proteins using the IMAC column for the following reason. Because the carboxylic acids have affinity to the IMAC column, peptides having acidic amino acids are more or less bound to the IMAC column.

In order to solve this problem, a purification method of digesting the proteins with trypsin and then methylesterifying the carboxylic acids in a methanol anhydride-hydrochloric acid solution so as to suppress the adsorption of the acidic amino acids to the IMAC column has been reported[13]. With this method, however, the phosphorylated proteins are, often times, not specifically purified for the following reasons[14]. The esterification does not quantitatively proceed, side effects occur, the selectivity is not improved as expected, or the peptides are insolubilized after the esterification.

In addition, dihydroxy benzoic acid (hereinafter, occasionally referred to simply as "DHB"), which is conventionally used for purifying phosphorylated proteins, is usable for MALDI-MS, but is not usable for LC-MS.

Under such a situation, it is difficult to detect phosphorylated proteins.

REFERENCE DOCUMENTS

1) Shou W, Verma R, Annan R S, Huddleston M J, Chen S L, Carr S A, Deshaies R J. Mapping phosphorylation sites in proteins by mass spectrometry. Methods Enzymol. 2002, 351:279-296.
2) McLachlin D T, Chait B T. Analysis of phosphorylated proteins and peptides by mass spectrometry. Curr Opin Chem Biol. 2001: 5, 591-602.
3) Gerard D, Tewis B. Global approaches to protein-protein interactions. Current Opinion in Cell Biology. 2003: 15(2), 199-205.
4) Watts J D, Affolter M, Krebs D L, Wange R L, Samelson L E, Aebersold R: Identification by electrospray ionization mass spectrometry of the sites of tyrosine phosphorylation induced in activated Jurkat T cells on the protein tyrosine kinase ZAP-70. J Biol Chem 1994, 269:29520-29529.
5) Michel H, Griffin P R, Shabanowitz J, Hunt D F, Bennett J.: Tandem mass spectrometry identifies sites of three post-translational modifications of spinach light-harvesting chlorophyll protein II. Proteolytic cleavage, acetylation, and phosphorylation. J Biol Chem. 1991, 266:17584-17591.
6) Neville D C, Rozanas C R, Price E M, Gruis D B, Verkman A S, Townsend R R: Evidence for phosphorylation of serine 753 in CFTR using a novel metal-ion affinity resin and matrix-assisted laser desorption mass spectrometry. Protein Sci 1997, 6:2436-2445.
7) Posewitz M C, Tempst P: Immobilized gallium(III) affinity chromatography of phosphopeptides. Anal Chem 1999, 71:2883-2892.
8) Wu X, Ranganathan V, Weisman D S, Heine W F, Ciccone D N, O'Neill T B, Crick K E, Pierce K A, Lane W S, Rathbun G, et al.: ATM phosphorylation of Nijmegen breakage syndrome protein is required in a DNA damage response. Nature 2000, 405:477-482.
9) Stensballe A, Andersen S, Jensen O N: Characterization of phosphoproteins from electrophoretic gels by nanoscale Fe(III) affinity chromatography with off-line mass spectrometry analysis. Proteomics 2001, 1:207-222.
10) Zhou W, Merrick B A, Khaledi M G, Tomer K B: Detection and sequencing of phosphopeptides affinity bound to immobilized metal ion beads by matrix-assisted laser desorption/ionization mass spectrometry. J Am Soc Mass Spectrom 2000, 11:273-282.
11) Nuwaysir L M, Stults J T: Electrospray ionization mass spectrometry of phosphopeptides isolated by on-line immobilized metal-ion affinity chromatography. J Am Soc Mass Spectrom 1993, 4:662-669.
12) Haydon C E, Eyers P A, Aveline-Wolf L D, Resing K A, Maller J L, Ahn N G.: Identification of Novel Phosphorylation Sites on Xenopus laevis Aurora A and Analysis of Phosphopeptide Enrichment by Immobilized Metal-affinity Chromatography. Mol Cell Proteomics 2003, 2:1055-1067.
13) Ficarro S B, McCleland M L, Stukenberg P T, Burke D J, Ross M M, Shabanowitz J, Hunt D F, White F M: Phosphoproteome analysis by mass spectrometry and its application to Saccharomyces cerevisiae. Nat Biotechnol. 2002, 20: 301-305.
14) Nuhse T S, Stensballe A, Jensen O N, Peck S C. Large-scale Analysis of in Vivo Phosphorylated Membrane Proteins by Immobilized Metal Ion Affinity Chromatography and Mass Spectrometry. Mol Cell Proteomics 2003, 2:1234-1243.

DISCLOSURE OF THE INVENTION

The present invention, made in light of such circumstances, has an object to be solved of detecting plural types of phosphorylated proteins in a sample (e.g., tissue, biological fluid, cell, cellular organ, or protein composite) with high precision in a short time period.

The present invention has another object of efficiently purifying one or plural types of phosphorylated proteins in a sample (e.g., tissue, biological fluid, cell, cellular organ, or protein composite).

In order to attain the above-described objects, the present inventors accumulated active studies and as a result, found that plural types of phosphorylated proteins in a sample (e.g., tissue, biological fluid, cell, cellular organ, or protein composite) can be detected with high precision in a short time period by: creating a database consisting of data regarding plural types of proteins in the sample, measuring the phosphorylated proteins separated from the sample with a mass spectrometer, and analyzing data obtained as a result of the measurement using the created database.

The present inventors also found that when purifying phosphorylated proteins with an immobilized metal carrier, by using a solution containing acetonitrile in a range of 40% (v/v) or greater but 60% (v/v) or less, and trifluoroacetic acid in a range of 0.1% (v/v) or greater but 1.0% (v/v) or less or hydrochloric acid in a range of 0.03% (v/v) or greater but 0.3% (v/v) or less, the non-specific adsorption is drastically decreased and one or plural types of phosphorylated proteins in a sample (e.g., tissue, biological fluid, cell, cellular organ, or protein composite) can be efficiently purified. Thus, the present inventors completed the present invention.

The present invention is directed to the following.

(1) A method for detecting plural types of phosphorylated proteins in a sample, wherein a database consisting of data regarding plural types of proteins in the sample is used.

(2) A method for detecting plural types of phosphorylated proteins in a sample, wherein a database consisting of data regarding plural types of proteins in the sample is used, the method comprising the steps of:
 (a) separating plural types of phosphorylated proteins from the sample;
 (b) analyzing a mass of the separated phosphorylated proteins; and
 (c) retrieving data obtained in step (b) from the database, thereby detecting the phosphorylated proteins.

(3) The method according to (1) or (2), wherein the database consisting of the data regarding the plural types of proteins in the sample is created by a process comprising the steps of:
 (a) analyzing a mass of the plural types of proteins in the sample;
 (b) identifying proteins from the obtained analysis result; and
 (c) creating the database consisting of the data regarding the identified proteins.

(4) The method according to (1) or (2), wherein the database consisting of the data regarding the plural types of proteins in the sample regards proteins identified by mass spectrometry on the plural types of proteins in the sample.

(5) A method for detecting plural types of phosphorylated proteins in a sample, wherein a database consisting of data regarding plural types of proteins in the sample is used, the method comprising the steps of:
 (a) analyzing a mass of the plural types of proteins in the sample;
 (b) identifying proteins from the obtained analysis result;
 (c) creating the database consisting of the data regarding the identified proteins;
 (d) separating plural types of phosphorylated proteins from the sample;
 (e) analyzing a mass of the separated phosphorylated proteins; and
 (f) retrieving the data obtained in step (e) from the database obtained in step (c), thereby detecting the phosphorylated proteins.

(6) The method according to any one of (1) through (5), wherein the sample is a tissue, a biological fluid, a cell, a cellular organ or a protein composite.

(7) The method according to any one of (2) through (6), wherein the step of separating plural types of phosphorylated proteins from the sample uses an immobilized metal carrier or a titania carrier and a solution containing acetonitrile in a range of 40% (v/v) or greater but 60% (v/v) or less.

(8) A method for purifying phosphorylated proteins using an immobilized metal carrier or a titania carrier, wherein a solution containing acetonitrile in a range of 40% (v/v) or greater but 60% (v/v) or less is used.

(9) A method for purifying phosphorylated proteins using an immobilized metal carrier or a titania carrier, wherein a solution containing acetonitrile in a range of 40% (v/v) or greater but 60% (v/v) or less is used as an equilibrating solvent for the immobilized metal carrier or the titania carrier, a solvent for dissolving the sample, and/or a developing solvent for the immobilized metal carrier or the titania carrier.

(10) A method for purifying phosphorylated proteins using an immobilized metal carrier or a titania carrier, the method comprising the steps of:

equilibrating the immobilized metal carrier or the titania carrier with a solution containing acetonitrile in a range of 40% (v/v) or greater but 60% (v/v) or less;

dissolving a sample in the solution containing acetonitrile in a range of 40% (v/v) or greater but 60% (v/v) or less;

putting the dissolved sample into contact with the equilibrated carrier; and eluting the phosphorylated proteins.

(11) The method according to any one of (8) through (10), wherein the solution containing acetonitrile in a range of 40% (v/v) or greater but 60% (v/v) or less further contains an acid.

(12) The method according to (11), wherein the acid is a strong acid.

(13) The method according to (12), wherein the strong acid is trifluoroacetic acid or hydrochloric acid.

(14) The method according to (13), wherein the trifluoroacetic acid has a concentration in a range of 0.1% (v/v) or greater but 1.0% (v/v) or less.

(15) The method according to (13), wherein the hydrochloric acid has a concentration in a range of 0.03% (v/v) or greater but 0.3% (v/v) or less.

(16) The method according to any one of (8) through (15), wherein metal ions immobilized to the immobilized metal carrier are iron ions (III) or gallium ions (III).

(17) The method according to any one of (8) through (16), which does not include dihydroxy benzoic acid.

(18) A kit for purifying phosphorylated proteins, comprising a solution containing acetonitrile in a range of 40% (v/v) or greater.

(19) The kit according to (18), which is used for a method according to any one of (8) through (17).

(20) A solution for purifying phosphorylated proteins, comprising a solution containing acetonitrile in a range of 40% (v/v) or greater.

(21) The solution according to (20), which is used for a method according to any one of (8) through (17).

According to the present invention, plural types of phosphorylated proteins in a sample (e.g., tissue, biological fluid, cell, cellular organ, or protein composite) can be detected with high precision, and the search time can be shortened.

According to the conventional method using an automatic search engine (e.g., MASCOT) and a protein database (e.g., NCBInr, EPI, or Sport), a great number of pseudopositive and pseudonegative results are provided and the search requires a huge amount of time. By creating a database consisting of data regarding plural types of proteins in a test sample as a target from which phosphorylated proteins are to be detected, measuring phosphorylated proteins separated from the sample with a mass spectrometer, and analyzing data obtained as a result of the measurement using the created database, plural types of phosphorylated proteins in the sample can be detected with high precision in a short time period. Types of phosphorylated proteins, which are not detectable by the conventional method, can now be detected.

According to the present invention, when purifying phosphorylated proteins with an immobilized metal carrier or a titania carrier, a solution containing acetonitrile in a range of 40% (v/v) or greater but 60% (v/v) or less, and preferably also containing a strong acid such as trifluoroacetic acid (e.g., in a range of 0.1% (v/v) or greater but 1.0% (v/v) or less) or hydrochloric acid (e.g., in a range of 0.03% (v/v) or greater but 0.3% (v/v) or less) is used. By using such a solution, the non-specific adsorption is drastically decreased and thus one or plural types of phosphorylated proteins in the sample (e.g., tissue, biological fluid, cell, cellular organ, or protein composite) can be efficiently purified.

With the conventional method, proteins having acidic amino acids are more or less bound to an IMAC column because carboxylic acids have affinity to the IMAC column. Therefore, it is not easy to purify only the phosphorylated proteins using the IMAC column. In addition, hydrophobic peptides, which have a non-specific action on IMAC, often cannot be removed. The method according to the present invention can suppress the adsorption of the carboxylic acids or hydrophobic substances to the IMAC column, and thus makes it possible to efficiently purify one or plural types of phosphorylated proteins in a sample (e.g., tissue, biological fluid, cell, cellular organ, or protein composite).

In addition, the problem of the purification method of methylesterifying carboxylic acids of proteins so as to suppress the adsorption of acidic amino acids to the IMAC column is now solved. Namely, the problem that specific purification is often impossible because the esterification does not quantitatively proceed, side reactions occur, the selectivity is not improved as expected, or the peptides are insolubilized after the esterification, is now solved. The method according to the present invention makes it possible to efficiently purify one or plural types of phosphorylated proteins in a sample (e.g., tissue, biological fluid, cell, cellular organ, or protein composite) without methylesterification.

The present invention does not require the use of DHB for purifying the phosphorylated proteins and thus does not require an operation of removing DHB.

Therefore, the purified sample can be measured with LC-MS in addition to MALDI-MS.

BRIEF DESCRIPTION OF THE DRAWINGS

FIG. 2 shows gi numbers and amino acid sequences represented in the FASTA format in an NCBInr database (gi|2853677, SEQ ID NO: 4; gi|2564245, SEQ ID NO: 5). A line starting with ">" represents the name of the protein, and the next line represents the amino acid sequence. A plurality of such pairs of lines is included in the database.

BEST MODE FOR CARRYING OUT THE INVENTION

Figure 1:
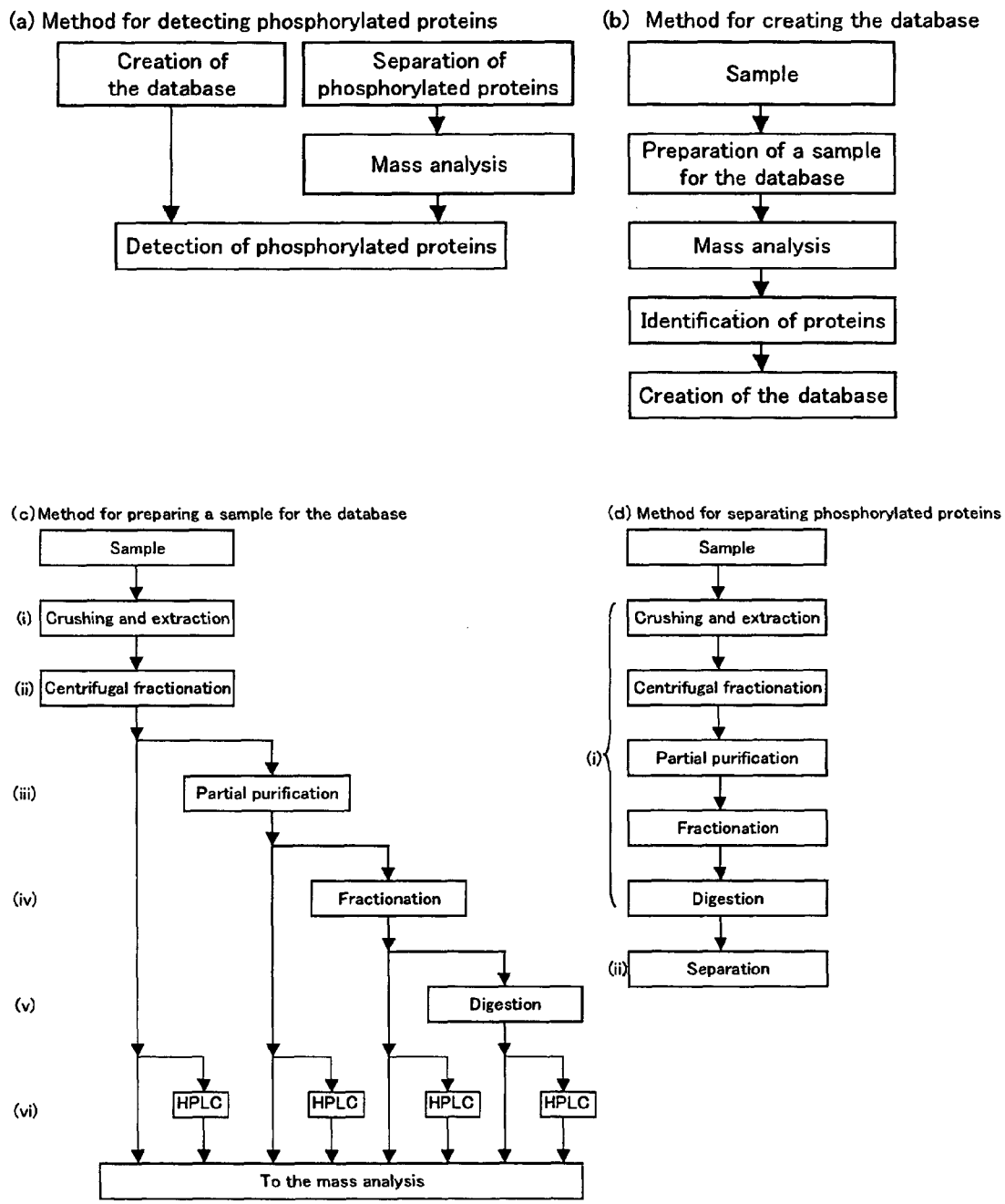
FIG. 1 is a schematic view of a method for detecting proteins according to the present invention.

Hereinafter, embodiments of the present invention will be described. The following embodiments are given in order to illustrate the present invention and are not intended to limit the present invention in any way. The present invention can be carried out in various embodiments without departing from the scope thereof.

The documents, laid-open publications, patents and other patent documents cited in this specification are incorporated herein by reference.

Herein, the term "protein" encompasses a peptide comprising two or more amino acids bound together by peptide binding.

Herein, the term "phosphorylated protein" refers to a protein in which one or more residual amino acid (e.g., tyrosine, serine, or threonine) is phosphorylated.

Herein, the term "sample" refers to a protein-containing detection target, preparation target, fractionation target or purification target. Preferably, the term "sample" refers to a tissue, a biological fluid, a cell, a cellular organ or a protein composite. A tissue is, for example, brain, a site of brain (e.g., olfactory bulb, amygdala nucleus, cerebral basal ganglia, hippocampus, thalamus, hypothalamus, cerebral cortex, medulla oblongata, or cerebellum), spinal cord, pituitary gland, stomach, pancreas, kidney, liver, gonad, thyroid gland, cholecystis, marrow, adrenal, cutis, muscle, lung, duodenum, small bowel, large bowel, blood vessel, heart, thymus, spleen, submandibular gland, parotid grand, sublingual gland, peripheral blood, prostate, testicle, ovarium, placenta, uterus, bone, joint, skeletal muscle, etc. A biological fluid is, for example, blood (including plasma and serum), urine, feces, saliva, tear fluid, infiltration fluid (including ascites and tissue fluid), etc. A cell is, for example, hepatocyte, splenic cell, neurocyte, gliacyte, pancreatic β cell, marrow cell, mesangial cell, Langerhans cell, epidermal cell, epithelial cell, goblet cell, endothelial cell, smooth muscular cell, fibroblast, fibrocyte, myocyte, adipocyte, immunocyte (e.g., macrophage, T cell, B cell, natural killer cell, mast cell, neutrophilic leukocyte, eosinophilic leukocyte, basophilic leukocyte, or monocyte), megakaryocyte, synovial cell, chondrocyte, osteocyte, osteoblast, osteoclast, mammary gland cell, interstitial cell, or precursor cell, stem cell or cancer cell thereof. A cellular organ is, for example, nucleus, organelle (nucleolus, karyotheca, cell membrane, mitochondrion, lysosome, ribosome, peroxisome, endoplasmic reticulum (granular endoplasmic reticulum, agulanular endoplasmic reticulum, sarcoplasmic reticulum, etc.), Golgi body, microtubule, centrosome, actin filament, etc.), cytosol, synapse, basal lamina, intercellular adhesion apparatus, etc. A protein composite includes two or more proteins physically bound together. The samples mentioned above are exemplary and the present invention is not limited to these.

The intended sample as mentioned above (e.g., tissue, biological fluid, cell, cellular organ, or protein composite) may be collected from an organism using a knife, a syringe or the like. In the case of a cell for use, an intended cell is collected from an organism and treated with an enzyme, or only an intended cell is selected by a cell sorter or the like. A cell usable as a sample encompasses a cell by primary culture, a cell line, or a cell cultured therefrom. A cell may be obtained in any of various culturing conditions such as stimulation or induction.

Herein, the term "database" refers to a collection of amino acid sequence information used for proteome analysis, in which the amino acid sequence information is systematized so as to be searched for by a computer. It is a routine technique to those skilled in the art when performing proteome analysis to search for amino acid sequence information using a database and a computer to identify a protein.

Herein, the expression "a database consisting of data regarding plural types of proteins in a sample" refers to a collection of amino acid sequence information of plural types of proteins in an intended sample, in which the amino acid sequence information is systematized so as to be searched for by a computer (hereinafter, such a database will occasionally be referred to as a "database of the present invention"). Accordingly, the database of the present invention may include letters and symbols for realizing systematic construction of the database, and also key information and protein names used for search, in addition to the amino acid sequence information.

A. Method for Detecting Phosphorylated Proteins

The present invention provides a method for detecting plural types of phosphorylated proteins in a sample, comprising the step of creating and using a database consisting of data regarding plural types of proteins in the sample.

This is a method for detecting phosphorylated proteins comprising the steps of: creating a database consisting of data regarding plural types of proteins in a sample; separating plural types of phosphorylated proteins from the sample; analyzing a mass of the separated phosphorylated proteins; and retrieving the obtained data from the database of the present invention and detecting the phosphorylated proteins (FIG. 1(a)).

Hereinafter, this will be described in detail.

1. Creation of a Database of the Present Invention

A database of the present invention may be created as follows. Proteins in a test sample as a target from which phosphorylated proteins are to be detected (hereinafter, also referred to as a "phosphorylated protein detection target sample") are prepared, a mass of the proteins is measured with a mass spectrometer, proteins are identified using the obtained data to acquire amino acid sequence information of the proteins, and the amino acid sequence information is systematized so as to be searched for using a computer (FIG. 2(b)). In the case where the amino acid sequence information of the proteins contained in the sample is found from known information without measurement, the amino acid sequence information is obtained, and the amino acid sequence information is systematized so as to be searched for using a computer.

Hereinafter, a method of measuring proteins in a phosphorylated protein detection target sample with a mass spectrometer, identifying proteins using the obtained data, and constructing a database from amino acid sequence information of the plural types of proteins will be described.

(1) Method for Preparing a Measurement Sample for Creating the Database of the Present Invention (FIG. 1(c))

A measurement sample for creating the database of the present invention may be prepared using a tissue, biological fluid, cell, cellular organ or protein composite of the same type as that of the phosphorylated protein detection target sample. Preferably, a measurement sample for creating the database of the present invention is prepared using a tissue, biological fluid, cell, cellular organ or protein composite, which is the same as the phosphorylated protein detection target sample.

An exemplary method for preparing a measurement sample is shown in FIG. 1(c), but the method is not limited to this.

A phosphorylated protein detection target sample is crushed, and a protein crude fluid may be extracted (FIG. (c)(i)) and then centrifugally fractionated (FIG. (c)(ii)). The resultant proteins will be referred to as "centrifugally fractionated proteins". A method of crushing and extraction is, for example, a method using a Downs-type Teflon™ homogenizer, a polytron, a warring blender, a Potter-type glass homogenizer, an ultrasonic crushing device or a cell-lysis solution (e.g., M-PER: Cat No. 78501, T-PER: Cat No. 78510, both produced by Pierce), or a freezing and thawing method. A method using a Downs-type Teflon™ homogenizer or a Potter-type glass homogenizer is preferable. A method of centrifugal fractionation is, for example, differential centrifugation or saccharose density gradient centrifugation. Saccharose density gradient centrifugation is preferable.

Next, when necessary, the centrifugally fractionated proteins may be partially purified (FIG. (c)(iii)). The resultant proteins will be referred to as "partially purified proteins". A method of partial purification is, for example, a method using group specific affinity column purification, cation exchange chromatography, anion exchange chromatography or reverse phase chromatography, immunoprecipitation, ammonium sulfate precipitation, precipitation by an organic solvent, ultrafiltration, gel filtration, dialysis, or a combination thereof. Group specific affinity column purification is preferable. In order to partially purify phosphorylated proteins or unphosphorylated proteins, an immobilized metal carrier described later (J Biol Chem 1994, 269:29520-29529, J Exp Med 2000, 192:1755-1762, Protein Sci 1997, 6:2436-2445, Anal Chem 1999, 71:2883-2892, Nature 2000, 405:477-482, Proteomics 2001, 1:207-222, J Am Soc Mass Spectrom 2000, 11:273-282, J Am Soc Mass Spectrom 1993, 4:662-69, J Biol Chem 2001, 276:6959-966, Nat Biotechnol. 2002: 20, 301-305, Proc Natl Acad Sci USA. 2003: 100, 443-448) or a titania carrier described later may be used. In the case where such a carrier is used, proteins adsorbing to the carrier are phosphorylated proteins, and proteins not adsorbing to the carrier are unphosphorylated proteins.

Each operation of crushing and extraction, centrifugal fractionation, and partial purification is not limited to the above-mentioned, and an appropriate technique may be selected or combined by the technological common sense of those skilled in the art.

Then, when necessary, the partially purified proteins may be fractionated and/or digested (FIG. 1(c)(iv), (v)). The resultant proteins will be respectively referred to as "fractionated proteins" and "digested proteins". A method of fractionation is, for example, two-dimensional electrophoresis, SDS-PAGE, or various types of chromatography (e.g., affinity chromatography, reverse phase chromatography, anion exchange chromatography, or cation exchange chromatography). The method is not limited to these, and an appropriate technique may be selected. A method of digestion is, for example, enzymatic digestion or chemical cleavage. Enzymatic digestion is preferable, but the method is not limited to these and an appropriate technique may be selected. An enzyme used for enzymatic digestion is, for example, trypsin, chemotrypsin, Lys-C, Asp-N or Glu-C. Trypsin is preferable. For enzymatic digestion, it is desirable to add a surfactant, preferably, 5-cyclohexyl-pentyl-beta-D-maltoside (U.S. Pat. No. 5,674,987 and U.S. Pat. No. 5,763,586, Anatrace Inc., Maumee, Ohio, USA).

The centrifugally fractionated proteins, partially purified proteins, fractionated proteins or digested proteins obtained above may be further fractionated by HPLC (FIG. 1(c)(vi)). The resultant proteins will be referred to as "HPLC fractionated proteins". For HPLC, an appropriate column may be selected by the technological common sense of those skilled in the art. An anion exchange column or a cation exchange column is preferable. Various conditions for HPLC (flow rate, detector, mobile phase, etc.) may be appropriately selected by the technological common sense of those skilled in the art.

In the case where the partially purified proteins are phosphorylated proteins partially purified with, for example, an immobilized metal carrier or a titania carrier, the phosphorylated proteins is digested and then the phosphorylated proteins or unphosphorylated proteins may be further fractionated with an immobilized metal carrier or a titania carrier. In other words, in order to selectively fractionate the unphosphorylated proteins, the immobilized metal carrier or titania carrier may be again used to fractionate proteins not adsorbing to the immobilized metal carrier or titania carrier from the proteins adsorbing to the immobilized metal carrier or titania carrier. Thus, unphosphorylated proteins can be obtained. The resultant proteins will be referred to as "fractionated unphosphorylated proteins". At this point, a small amount of (e.g., 0.01% to 20%) of phosphorylated proteins may be mixed. Even if such a small amount of phosphorylated proteins is mixed, the measurement result of the unphosphorylated proteins is not influenced almost at all.

The unphosphorylated proteins have the following two uses.

First, by the method of separating phosphorylated proteins from the proteins existing in a phosphorylated protein detection target sample, phosphorylated proteins and unphosphorylated proteins are separated from each other. Using the unphosphorylated proteins, a database is created. Using the phosphorylated proteins, phosphorylated proteins are detected.

Second, by the method of separating phosphorylated proteins from the proteins existing in a phosphorylated protein detection target sample, phosphorylated proteins are separated. The phosphorylated proteins are digested to prepare the phosphorylated proteins (peptides) and unphosphorylated proteins (peptides). The unphosphorylated proteins (peptides) are measured to create a database. Using the phosphorylated proteins (peptides), phosphorylated proteins are detected. As the unphosphorylated proteins (peptides), the above-mentioned "fractionated unphosphorylated proteins" may be used. The database only includes phosphorylated proteins among the proteins contained in the sample, and so is especially useful for the detection method of the present invention.

(2) Method for Measuring a Mass of a Measurement Sample for Creating the Database of the Present Invention Next, a mass of the proteins contained in the measurement sample obtained by the above-described operation (i.e., the centrifugally fractionated proteins, the partially purified proteins, the separated proteins, the digested proteins, the HPLC separated proteins, or the separated unphosphorylated proteins) is measured with a mass spectrometer. As the spectrometer, a general-purpose device is usable, such as a gas chromatography mass spectrometry (GC/MS) device, which is a mass spectrometer combined with a gas chromatography device, or a liquid chromatography mass spectrometry (LC/MS) device, which is a mass spectrometer combined with a liquid chromatography device. An ionization method used by the mass spectrometer may be appropriately selected in accordance with the device to be used. A usable ionization method is, for example, MALDI (matrix-assisted laser desorption/ionization), ESI (electrospray ionization), EI (electron impact ionization), CI (chemical ionization), APCI (atmospheric pressure chemical ionization), FAB (fast atom bombardment), LD, FD, SIMS, or TSP. MALDI or ESI is preferable. An analyzer may be appropriately selected in accordance with the device to be used. For example, a general-purpose device of TOF (time of flight) type, ion trap type, double-focusing type, quadruple pole type, Fourier transformation type or the like is usable. The device and method for mass spectrometry are not limited to those mentioned above, and a device and a method usually used by those skilled in the art may be appropriately selected.

(3) Method for Identifying Proteins

Using the data obtained as a result of measurement performed with a mass spectrometer, proteins may be identified. Namely, the obtained data may be analyzed using software (e.g., SonarMSMS (produced by Genomic Solution) and a database (e.g., NCBInr (http://www.ncbi.nlm.nih.gov/), IPI, or Sport) so as to identify proteins in the sample. It is easy to those skilled in the art to identify proteins using the measurement data obtained with a mass spectrometer (Nat Genet. 1998: 20, 46-50; J Cell Biol. 1998: 141, 967-977; J Cell Biol. 2000: 148, 635-51; Nature. 2002: 415, 141-147; Nature. 2002: 415, 180-183; Curr Opin Cell Biol. 2003: 15, 199-205; Curr Opin Cell Biol. 2003: 7, 21-27). It is easy to those skilled in the art to obtain amino acid sequence information from the information on the identified proteins.

(4) Method for Creating the Database

The obtained plural pieces of amino acid sequence information are systematized so as to be searched for by a computer. The amino acid sequence information used for the creation of the database may be a combination of plural pieces of amino acid sequence information obtained from samples prepared by different methods.

Herein, the term "systematize" refers to providing the obtained plural pieces of amino acid sequence information in an orderly and uniform manner so as to be usable by a computer.

The database of the present invention may be in any format as long as the amino acid sequence information of the identified proteins in the phosphorylated protein detection target sample is systematized so as to be searched for by a computer.

The database of the present invention may be created by systematizing the amino acid sequence information of the identified proteins in the phosphorylated protein detection target sample so as to be searched for by a computer.

Hereinafter, an exemplary method for creating the database of the present invention will be described.

Identified proteins each necessarily include unique key information such that the used database is accessible. For example, the key information is a gi number for the NCBInr database.

The database format usually used by protein identification software is called FASTA format. With FASTA format, data is described with the following rule. A line starting with ">" represents the name of the protein, and the next line represents the amino acid sequence (FIG. 2). A plurality of such pairs of lines is included in the database.

From the protein information identified by the protein identification software, key information comprising gi numbers (gi|XXXXXX) (gi|2853677, SEQ ID NO: 4) (gi|2564245, SEQ ID NO: 5) is retrieved, and a search is made in the database defined by the FASTA format. A line defining the protein name which is partially matched to the key information, and the next line defining the amino acid sequence, are retrieved. This is performed for all the identified proteins, and a database consisting of only the identified proteins is newly created in the FASTA format.

This database is registered in the protein identification software. Thus, proteins become searchable in this database.

As described above, the database of the present invention is for proteins identified by mass spectrometry of plural types of proteins in a sample. The database of the present invention may be created by measuring a mass of the proteins in a phosphorylated protein detection target sample with a mass spectrometer, identifying proteins using the obtained data to acquire amino acid sequence information of the proteins, and systematizing the amino acid sequence information so as to be searched for using a computer.

An identical type of tissue, biological fluid, cell, cellular organ or protein composite is considered to express an identical protein. Therefore, for such an identical type of tissue, biological fluid, cell, cellular organ or protein composite, the database of the present invention does not need to be created for each test and is usable repeatedly in a plurality of tests.

2. Separation of Phosphorylated Proteins

Next, a method for separating phosphorylated proteins from a phosphorylated protein detection target sample will be described.

(1) Method for Preparing Phosphorylated Proteins (FIG. 1(d)(i))

Like the method for preparing a measurement sample described above, a phosphorylated protein detection target sample is crushed, and proteins are treated with extraction, centrifugal fractionation, partial purification, fractionation, digestion, or a combination thereof. Thus, digested proteins can be obtained. According to the present invention, phosphorylated proteins are preferably prepared by crushing a sample, and extracting, centrifugally fractionating, partially purifying, fractionating and digesting the proteins. FIG. 1(d)(i) shows only one embodiment of the method for preparing phosphorylated proteins, and the method is not limited to this.

(2) Method for Separating Phosphorylated Proteins (FIG. 1(d)(ii))

From the digested proteins, phosphorylated proteins are further separated. The resultant proteins will be referred to as "separated phosphorylated proteins". Separation of the phosphorylated proteins may be performed by any method which can selectively separate the phosphorylated proteins. A usable method is, for example, a separation method using an immobilized metal carrier or a titania carrier, or immunoprecipitation using an antiphosphorylation antibody. A separation (purification) method using an immobilized metal carrier or a titania carrier which will be described later in the section of "B. Method for purifying phosphorylated proteins" is preferable.

The method for separating phosphorylated proteins using an immobilized metal carrier or a titania carrier is performed as follows. First, the immobilized metal carrier or the titania carrier is equilibrated with a solution containing acetonitrile. Next, the proteins prepared by the operation of (1) are dissolved in the acetonitrile-containing solution. Then, the proteins dissolved in the solution, and the immobilized metal carrier or the titania carrier equilibrated with the solution, are put into contact with each other. After this, it is desirable to wash the immobilized metal carrier or the titania carrier with the acetonitrile-containing solution. Phosphorylated proteins are eluted with an appropriate elution solution. There is no specific limitation regarding the elution solution. A usable elution solution is, for example, 150 mM ammonia water containing 5% (v/v) acetonitrile or 0.1% phosphoric acid containing 5% (v/v) acetonitrile. In the case where the phosphorylated proteins are eluted with ammonia water, it is desirable to dry the elution solution as it is. In the case where the phosphorylated proteins are eluted with phosphoric acid, it is desirable to perform desalting.

In each operation of equilibrated, dissolution and washing, the acetonitrile concentration in the acetonitrile-containing solution is 30% (v/v) or greater but 70% (v/v) or less, preferably 35% (v/v) or greater but 65% (v/v) or less, more preferably 40% (v/v) or greater but 60% (v/v) or less, and especially preferably 45% (v/v) or greater but 55% (v/v) or less, for example, 50% (v/v). To this solution, an acid solution may be added. A preferably usable acid solution is, for example, of a strong acid, for example, trifluoroacetic acid or hydrochloric acid. A trifluoroacetic acid solution is especially preferable, but there is no specific limitation. The concentration of the acid solution in the acetonitrile-containing solution is as follows. In the case of trifluoroacetic acid, the concentration is preferably 0.1% (v/v) or greater but 1.0% (v/v) or less, and especially preferably 0.2% (v/v) or greater but 0.6% (v/v) or less, for example, 0.3% (v/v). In the case of hydrochloric acid, the concentration is preferably 0.03% (v/v) or greater but 0.3% (v/v) or less, and especially preferably 0.06% (v/v) or greater but 0.2% (v/v) or less, for example, 0.1% (v/v).

The phosphorylated proteins can be separated as described above.

3. Measurement of the Phosphorylated Proteins with a Mass Spectrometer

Next, the separated phosphorylated proteins are measured with a mass spectrometer. As the spectrometer, a general-purpose device is usable such as a gas chromatography mass spectrometry (GC/MS) device, which is a mass spectrometer combined with a gas chromatography device, or a liquid chromatography mass spectrometry (LC/MS) device, which is a mass spectrometer combined with a liquid chromatography device. It is preferable to use the liquid chromatography mass spectrometry device. An ionization method used by the mass spectrometer may be appropriately selected in accordance with the device to be used. A usable ionization method is, for example, MALDI (matrix-assisted laser desorption/ionization), ESI (electrospray ionization), EI (electron impact ionization), CI (chemical ionization), APCI (atmospheric pressure chemical ionization), FAB (fast atom bombardment), LD, FD, SIMS, or TSP. MALDI or ESI is preferable. An analyzer may be appropriately selected in accordance with the device to be used. For example, a general-purpose device of TOF (time of flight) type, ion trap type, double-focusing type, quadruple pole type, Fourier transformation type or the like is usable. The device and method for mass spectrometry are not limited to those mentioned above, and a device and a method usually used by those skilled in the art may be appropriately selected.

4. Data Analysis and Detection of Phosphorylated Proteins

As the database for data analysis, the database of the present invention is used.

The data obtained as a result of the measurement performed with a mass spectrometer is analyzed using software (e.g., MASCOT produced by Matrix Science) and the database of the present invention, and thus phosphorylated proteins in the sample can be identified.

Regarding the obtained results, it is preferable to manually confirm the mass spectra one by one, but the present invention is not limited to this. In the case where the phosphorylated amino acids are serine or threonine, it is preferable that a peak distanced from the peak of the parent ions (peak of unphosphorylated proteins) by 98 Da is clearly observed (in the case of ion-trap ESI-MS, very strongly observed). In the case where the phosphorylated amino acids are tyrosine, it is preferable that a peak distanced from the peak of the parent ions by 80 Da is clearly observed. Such determination criteria can be easily assumed by those skilled in the art.

By such a method, phosphorylated proteins can be detected efficiently, and the search time can be significantly shortened.

B. Method for Purifying Phosphorylated Proteins

The present invention provides a method for purifying phosphorylated proteins using an immobilized metal carrier or a titania carrier, wherein a solution containing acetonitrile in a range of 40% (v/v) or greater but 60% (v/v) or less is used.

Hereinafter, this will be described in detail.

1. Immobilized Metal Carrier or Titania Carrier

Herein, the term "immobilized metal carrier" refers to a carrier having metal ions chelate-bound to a chelate-forming group (e.g., iminodiacetic acid group (hereinafter, occasionally referred to as "IDA") or nitrilotriacetic acid group (hereinafter, occasionally referred to as "NTA")). An immobilized metal carrier is, for example, an iron ion (III) carrier having chelate-bound iron ions (III) or a gallium (III) carrier having chelate-bound gallium ions (III).

A usable carrier is, for example, agarose gel, acrylamide, magnetic beads, or cellulose. Agarose gel is preferable.

An immobilized metal carrier may be produced by chelate-binding appropriate metal ions, preferable iron ions (III) or gallium ions (III) to a chelate-forming group (e.g., IDA or NTA).

A carrier having a chelate-forming group (e.g., IDA or NTA) is available from, for example, Amersham Biosciences (Chelating Sepharose Fast Flow, produced by Amersham Biosciences, Cat No. 17-0575-01).

An iron ion (III) carrier may be produced by, for example, washing a carrier having a chelate-forming group (e.g., IDA or NTA) with 0.1% acetic acid water, next mixing the resultant carrier with 50 mM iron chloride III ($FeCl_3$) dissolved in 0.1% acetic acid, and then washing the resultant substance with 0.1% acetic acid water.

A carrier having a chelate-forming group is also available from Sigma-Aldrich (PHOS-Selec Iron Affinity Gel, produced by Sigma-Aldrich, Cat No. P9740).

A gallium ion (III) carrier may be produced by, for example, washing a carrier having a chelate-forming group (e.g., IDA or NTA) with 0.1% acetic acid water, next mixing the resultant carrier with 50 mM gallium chloride III ($GaCl_3$) dissolved in 0.1% acetic acid, and then washing the resultant substance with 0.1% acetic acid water.

This carrier is also available from Pierce (Phosphopeptide Isolation Kit, produced by Pierce, Cat No. 89853).

An immobilized metal carrier is usable as an immobilized metal affinity chromatography column (IMAC column) by being caused to fill an appropriate column (e.g., Polyprep empty column (produced by BioRad, Cat No. 731-1550)). An immobilized metal carrier is also usable by being put to an appropriate tube (e.g., Eppendorf Tube (produced by Eppendorf)).

Herein, the term "titania" refers to titanium dioxide (IV) ($TiO_2$). Herein, the term "titania carrier" refers to a spherical bead of titania having a diameter of about several to several tens of micrometers. A titania carrier is available from GL Sciences.

A titania carrier is usable as a titania column by being caused to fill an appropriate column (e.g., Micro Biospin empty column (produced by BioRad, Cat No. 732-6204)). A titania carrier is also usable by being put to an appropriate tube (e.g., Eppendorf Tube (produced by Eppendorf)).

2. Purifying Solution of the Present Invention

In a method for purifying phosphorylated proteins with the immobilized metal carrier or the titania carrier according to the present invention, a solution containing acetonitrile in a range of 40% (v/v) or greater but 60% (v/v) or less (hereinafter, such a solution will occasionally be referred to as a "purifying solution of the present invention") is used.

Acetonitrile may be commercially available from, for example, Wako Pure Chemical Industries, Ltd.

A purifying solution of the present invention is used for the immobilized metal carrier or the titania carrier. More practically, a purifying solution of the present invention is used as, for example, an equilibrating solvent for the immobilized metal carrier or the titania carrier, a solvent for dissolving a sample, and/or a developing solvent for the immobilized metal carrier or the titania carrier. The concentration of acetonitrile in the purifying solution of the present invention is at least 30% (v/v) or greater but 70% (v/v) or less, preferably 35% (v/v) or greater but 65% (v/v) or less, more preferably 40% (v/v) or greater but 60% (v/v) or less, and especially preferably 45% (v/v) or greater but 55% (v/v) or less, for example, 50% (v/v). The purifying solution of the present invention may contain other substances.

In the purifying solution of the present invention, an acid solution may be included. A preferably usable acid solution is, for example, of a strong acid, for example, trifluoroacetic acid or hydrochloric acid. A trifluoroacetic acid solution is especially preferable, but there is no specific limitation. The concentration of the acid solution in the purifying solution is as follows. In the case of trifluoroacetic acid, the concentration is preferably 0.1% (v/v) or greater but 1.0% (v/v) or less, and especially preferably 0.2% (v/v) or greater but 0.6% (v/v) or less, for example, 0.3% (v/v). In the case of hydrochloric acid, the concentration is preferably 0.03% (v/v) or greater but 0.3% (v/v) or less, and especially preferably 0.06% (v/v) or greater but 0.2% (v/v) or less, for example, 0.1% (v/v). Such a purifying solution of the present invention could be easily prepared by those skilled in the art.

Trifluoroacetic acid may be commercially available from, for example, Pierce.

Hydrochloric acid may be commercially available from, for example, Wako Pure Chemical Industries, Ltd.

3. Phosphorylated Proteins

According to the present invention, proteins to be purified may be of any type which contains phosphorylated proteins. Proteins extracted from a sample (e.g., tissue, biological fluid, cell, cellular organ, or protein composite) are preferable.

Hereinafter, a method for purifying phosphorylated proteins in a sample will be described.

(1) Method for Preparing Proteins in a Sample

A sample is crushed, and a protein crude fluid may be extracted and then centrifugally fractionated. The resultant proteins will be referred to as "centrifugally fractionated proteins". A method of crushing and extraction is, for example, a method using a Downs-type Teflon™ homogenizer, a polytron, a warring blender, a Potter-type glass homogenizer, an ultrasonic crushing device or a cell-lysis solution (e.g., M-PER: Cat No. 78501, T-PER: Cat No. 78510, both produced by Pierce), or a freezing and thawing method. A method using a Downs-type Teflon™ homogenizer or a Potter-type glass homogenizer is preferable. A method of centrifugal fractionation is, for example, differential centrifugation or saccharose density gradient centrifugation. Saccharose density gradient centrifugation is preferable.

Next, when necessary, the centrifugally fractionated proteins may be partially purified. The resultant proteins will be referred to as "partially purified proteins". A method of partial purification is, for example, a method using group specific affinity column purification, cation exchange chromatography, anion exchange chromatography or reverse phase chromatography, immunoprecipitation, ammonium sulfate precipitation, precipitation by an organic solvent, ultrafiltration, gel filtration, dialysis, or a combination thereof. Group specific affinity column purification is preferable. Each operation of crushing and extraction, centrifugal fractionation, and partial purification is not limited to the above-mentioned, and an appropriate technique may be selected or combined by the technological common sense of those skilled in the art.

Then, when necessary, the partially purified proteins may be fractionated and digested. The resultant proteins will be respectively referred to as "fractionated proteins" and "digested proteins". A method of fractionation is, for example, two-dimensional electrophoresis, SDS-PAGE, or various types of chromatography (e.g., affinity chromatography, reverse phase chromatography, anion exchange chromatography, or cation exchange chromatography), but the method is not limited to these and an appropriate technique may be selected. A method of digestion is, for example, enzymatic digestion or chemical cleavage. Enzymatic digestion is preferable, but the method is not limited to these and an appropriate technique may be selected. An enzyme used for enzymatic digestion is, for example, trypsin, chemotrypsin, Lys-C, Asp-N or Glu-C. Trypsin is preferable. For enzymatic digestion, it is desirable to add a surfactant, preferably, 5-cyclohexyl-pentyl-beta-D-maltoside (U.S. Pat. No. 5,674,987 and U.S. Pat. No. 5,763,586, Anatrace Inc., Maumee, Ohio, USA).

The centrifugally fractionated proteins, partially purified proteins, fractionated proteins or digested proteins obtained above may be further fractionated by HPLC. The resultant proteins will be referred to as "HPLC fractionated proteins". For HPLC, an appropriate column may be selected by the technological common sense of those skilled in the art. An anion exchange column or a cation exchange column is preferable. Various conditions for HPLC (flow rate, detector, mobile phase, etc.) may be appropriately selected by the technological common sense of those skilled in the art.

(2) Method for Purifying Phosphorylated Proteins

Next, the proteins obtained by the above-described operation (i.e., centrifugally fractionated proteins, partially purified proteins, fractionated proteins, digested proteins, HPLC fractionated proteins, or separated unphosphorylated proteins) are purified with an immobilized metal carrier or a titania carrier.

Hereinafter, a method for purification will be described in detail.

First, the immobilized metal carrier or the titania carrier is equilibrated with a purifying solution of the present invention. In the case where an appropriate column is filled with the immobilized metal carrier or the titania carrier, the step of equilibration may be performed by applying the purifying solution of the present invention to the column. In the case where the immobilized metal carrier or the titania carrier is put to an appropriate tube, the step of equilibration may be performed by adding the purifying solution of the present invention to the tube.

Next, the proteins obtained by the above-described operation are dissolved in the purifying solution of the present invention. In the case where the proteins are dissolved in a solvent, a concentrated purifying solution of the present invention may be diluted for use. At this point, the concentration of acid in the purifying solution of the present invention may be adjusted in accordance with the solute contained in the solvent.

The final concentration of the acid solution is as follows. In the case of trifluoroacetic acid, the concentration is preferably 0.1% (v/v) or greater but 1.0% (v/v) or less, and especially preferably 0.2% (v/v) or greater but 0.6% (v/v) or less, for example, 0.3% (v/v). In the case of hydrochloric acid, the concentration is preferably 0.03% (v/v) or greater but 0.3% (v/v) or less, and especially preferably 0.06% (v/v) or greater but 0.2% (v/v) or less, for example, 0.1% (v/v).

Next, the proteins dissolved in the purifying solution of the present invention, and the immobilized metal carrier or the titania carrier equilibrated with the purifying solution of the present invention, are put into contact with each other. In the case where an appropriate column is filled with the immobilized metal carrier or the titania carrier, the step of putting the proteins dissolved in the purifying solution of the present invention, and the immobilized metal carrier or the titania carrier equilibrated with the purifying solution of the present invention, into contact with each other may be performed by applying the proteins dissolved in the purifying solution of the present invention to the column. In the case where the immobilized metal carrier or the titania carrier is put to an appropriate tube, such a step may be performed by adding the proteins dissolved in the purifying solution of the present invention to the tube.

Then, it is desirable to wash the immobilized metal carrier or the titania carrier with the purifying solution of the present invention. In the case where an appropriate column is filled with the immobilized metal carrier or the titania carrier, the washing operation may be performed by adding the purifying solution of the present invention to the column. In the case where the immobilized metal carrier or the titania carrier is put to an appropriate tube, the washing operation may be performed by adding the purifying solution of the present invention to the tube and conducting a centrifugal operation.

After this, phosphorylated proteins are eluted with an appropriate elution solution. In the case where an appropriate column is filled with the immobilized metal carrier or the titania carrier, the step of eluting the phosphorylated proteins may be performed by applying an appropriate elution solution to the column. In the case where the immobilized metal carrier or the titania carrier is put to an appropriate tube, such a step may be performed by adding an appropriate elution solution to the tube and conducting a centrifugal operation. There is no specific limitation regarding the elution solution. A usable elution solution is, for example, 150 mM ammonia water containing 5% (v/v) acetonitrile or 0.1% phosphoric acid containing 5% (v/v) acetonitrile. In the case where the phosphorylated proteins are eluted with ammonia water, it is desirable to dry the elution solution as it is. In the case where the phosphorylated proteins are eluted with phosphoric acid, it is desirable to perform desalting.

By such a method, phosphorylated proteins can be purified efficiently. The phosphorylated proteins thus obtained are usable for various tests, preferably for analyzing the phosphorylated proteins with MS.

4. Kit for Purifying Phosphorylated Proteins

The present invention provides a kit for purifying phosphorylated proteins, which comprises a solution being used for a method for purifying phosphorylated proteins using an immobilized metal carrier or a titania carrier and using a solution containing acetonitrile in a range of 40% (v/v) or greater but 60% (v/v) or less (hereinafter, such a kit will be occasionally referred to as a "purifying kit of the present invention").

The purifying kit of the present invention is used for the method for purifying phosphorylated proteins (described in "B.3.(2) Method for purifying phosphorylated proteins".

A carrier, solution and the like included in the purifying kit of the present invention are, for example, as follows.

(i) an immobilized metal carrier or a titania carrier;
(ii) a solution containing acetonitrile in a range of 40% (v/v) or greater;
(iii) an acid, preferably a strong acid, for example, trifluoroacetic acid or hydrochloric acid, especially preferably trifluoroacetic acid; and
(iv) other necessary solutions (e.g., PBS, Tris buffer solution).

A solution containing acetonitrile in a range of 40% (v/v) or greater may have an acid, preferably a strong acid, for example, trifluoroacetic acid or hydrochloric acid, especially preferably trifluoroacetic acid, incorporated thereinto beforehand.

The purifying kit of the present invention may further include a tube, a column, a vessel, an operation manual and the like necessary for the purification.

5. Solution for Purifying Phosphorylated Proteins

The present invention provides a solution for purifying phosphorylated proteins, which comprises a solution being used for a method for purifying phosphorylated proteins using an immobilized metal carrier or a titania carrier and using a solution containing acetonitrile in a range of 40% (v/v) or greater but 60% (v/v) or less (hereinafter, such a purifying solution will be occasionally referred to as a "phosphorylated protein purifying solution of the present invention").

The phosphorylated protein purifying solution of the present invention is used for the method for purifying phosphorylated proteins (described in "B.3.(2) Method for purifying phosphorylated proteins".

The phosphorylated protein purifying solution of the present invention contains acetonitrile in a range of 40% (v/v) or greater, and may have an acid, preferably a strong acid, for example, trifluoroacetic acid or hydrochloric acid, especially preferably trifluoroacetic acid, incorporated thereinto beforehand.

Hereinafter, the present invention will be described by way of specific examples, but the present invention is not limited to these examples.

Reference Example 1

A Post Synaptic Density (hereinafter, referred to as "PSD") fraction was prepared from the brain of a mouse by the following operation.

The whole brain was taken out from a seven weeks old BALB/c (female), ice-cooled PBS (containing protease cocktail; Roche: 1873580) was added thereto, and the whole brain was finely ground by a Teflon™-coated glass homogenizer. A solid content was removed as follows. The ground brain was centrifuged at 1400 G for 10 minutes to remove the precipitate. The supernatant was centrifuged at 13800 G for 16 minutes to collect the precipitate. The precipitate was suspended with 0.32 M sucrose. The sucrose was stacked in 1.2 M, 1 M and 0.85 M layers sequentially from the bottom, and the suspended sample was put on the top layer and centrifuged at 82500 G for 120 minutes. The fraction existing in the second layer from the bottom (Synaptosome) was collected and suspended with 0.32 M sucrose. Then, 6 mM Tris buffer solution was added thereto, and the resultant substance was stirred while being cooled with ice for 45 minutes. After this, the resultant substance was centrifuged at 32800 G for 20 minutes to collect the precipitate. The precipitate was suspended with 0.32 M sucrose. The sucrose was stacked in 0.8 M, 0.6 M and 0.4 M layers sequentially from the bottom, and the suspended sample was put on the top layer and centrifuged at 64700 G for 120 minutes. The second layer from the bottom was taken out and centrifuged at 48200 G for 30 minutes. To the resultant precipitate, a Tris buffer solution—0.32 M sucrose mixture solution containing 1% Triton X-100 was added, and the resultant substance was stirred for 15 minutes. The resultant substance was centrifuged at 48200 G for 30 minutes to collect the precipitate. The collected precipitate was set to be used as the PSD fraction.

The PSD fraction was dissolved in 7 M urea—2 M thiourea—2% 1 CHAPS. The dissolved protein was treated with digestion, fractionation and analysis in the following combinations.

The precipitate was dissolved in SDS, and the proteins were fractionated with SDS-PAGE. Then, the resultant proteins were digested with trypsin in a gel, and analyzed with LC/MS/MS using a C18 column.

1) Digested with trypsin, and then fractionated with a cation exchange column (produced by Amersham; hereinafter, referred to as an "SCX column"). Each fraction was analyzed with LC/MS/MS (Finnigan, LCQ) using a C18 column (hereinafter, referred to as "digestion—SCX column—LC/MS/MS").

2) Digested with trypsin, and then fractionated with a cyanopropyl column (produced by YMC; hereinafter, referred to as a "CN column"). Each fraction was analyzed with LC/MS/MS (Finnigan, LCQ) using a C18 column (hereinafter, referred to as "digestion—CN column—LC/MS/MS").

3) Digested with trypsin, and then fractionated with an anion exchange column (produced by Amersham; hereinafter, referred to as an "SAX column"). Each fraction was analyzed with LC/MS/MS (Finnigan, LCQ) using a C18 column (hereinafter, referred to as "digestion—SAX column—LC/MS/MS").

4) Digested with trypsin, fractionated with an SAX column, and then further fractionated with a CN column. Each fraction was analyzed with LC/MS/MS (Finnigan, LCQ) using a C18 column (hereinafter, referred to as "digestion—SAX column—CN column—LC/MS/MS").

5) The proteins were fractionated with SDS-PAGE, digested with trypsin in a gel, and analyzed with LC/MS/MS (Finnigan, LCQ) using a C18 column (hereinafter, referred to as "SDS-PAGE (protein fractionation)—digestion—LC/MS/MS").

6) The proteins were fractionated with a MonoQ column (produced by Amersham). Each fraction was digested with trypsin and then fractionated with an SCX column. Each fraction was analyzed with LC/MS/MS (Finnigan, LCQ) using a C18 column (hereinafter, referred to as "MonoQ column (protein fractionation)—digestion—SCX column—LC/MS/MS").

7) The proteins were fractionated with a MonoQ column (produced by Amersham). Each fraction was digested with trypsin and then fractionated with an SAX column. Each fraction was analyzed with LC/MS/MS (Finnigan, LCQ) using a C18 column (hereinafter, referred to as "MonoQ column (protein fractionation)—digestion—SAX column—LC/MS/MS").

8) The proteins were fractionated with a MonoQ column (produced by Amersham). Each fraction was digested with trypsin and then fractionated with a CN column. Each fraction was analyzed with LC/MS/MS (Finnigan, LCQ) using a C18 column (hereinafter, referred to as "MonoQ column (protein fractionation)—digestion—CN column—LC/MS/MS").

9) The proteins were fractionated with a MonoQ column (produced by Amersham), fractionated with SDS-PAGE, then digested with trypsin in a gel, and analyzed with LC/MS/MS (Finnigan, LCQ) using a C18 column (hereinafter, referred to as "MonoQ column (protein fractionation)—SDS-PAGE (protein fractionation)—digestion—LC/MS/MS").

10) The proteins were fractionated with a MonoQ column (produced by Amersham), digested with trypsin, fractionated with an SAX column, and then further fractionated with a CN column. Each fraction was analyzed with LC/MS/MS (Finnigan, LCQ) using a C18 column (hereinafter, referred to as "MonoQ column (protein fractionation)—digestion—SAX column—CN column—LC/MS/MS").

11) The precipitate was dissolved in SDS, and the proteins were fractionated with SDS-PAGE, then digested with trypsin in a gel, and analyzed with LC/MS/MS (Finnigan, LCQ) using a C18 column (hereinafter, referred to as "precipitate—SDS-PAGE (protein fractionation)—digestion—LC/MS/MS").

As a result, the following number of proteins were identified. By 1) digestion—SCX column—LC/MS/MS, 108 proteins; by 2) digestion—CN column—LC/MS/MS, 94 proteins; by 3) digestion—SAX column—LC/MS/MS, 212 proteins; by 4) digestion—SAX column—CN column—LC/MS/MS, 376 proteins, by 5) SDS-PAGE (protein fractionation)—digestion—LC/MS/MS, 92 proteins; by 6) MonoQ column (protein fractionation)—digestion—SCX column—LC/MS/MS, 140 proteins; by 7) MonoQ column (protein fractionation)—digestion—SAX column—LC/MS/MS, 301 proteins; by 8) MonoQ column (protein fractionation)—digestion—CN column—LC/MS/MS, 199 proteins; by 9) MonoQ column (protein fractionation)—SDS-PAGE (protein fractionation)—digestion—LC/MS/MS, 233 proteins; by 10) MonoQ column (protein fractionation)—digestion—SAX column—CN column—LC/MS/MS, 450 proteins; and by 11) precipitate—SDS-PAGE (protein fractionation)—digestion—LC/MS/MS, 152 proteins. Excluding overlapping proteins, 888 proteins were identified (LC/MS/MS was performed a total of 1150 times; the number of identified peptides (unmodified) was 10592).

By this experiment, a huge number of peptides were analyzed. It was considered that peptides which were not identified by the analysis included phosphorylated peptides. Therefore, phosphomodified proteins were searched for, using an automatic search engine MASCOT (produced by Matrix Science) and the NCBInr database.

Practically, the protein data of a device NCBInr was saved in a PC server (Windows 2000 Server) of ProLiant ML530 (Compaq; hard disc capacity: 425 GB; memory capacity: 3.767828 GB; CPU: Intel™ XEON™ 2.40 GHz; number of logical CPUs: 4). All the LC/MS/MS data obtained by the analysis described above was also saved in this PC server. The phosphorylated proteins included in the measurement samples used for the measurement performed 1150 times were searched for, using the automatic search engine MASCOT installed in the PC server. The search conditions were as follows. Oxidation(M), Phospho(ST), and Phospho(Y) were designated as Variable Modification; the number of missed cleavages was set to 2; and NCBInr was designated as the database. The number of missed cleavages was set to 2 because it is empirically found that phosphorylated peptides have a low digestion efficiency by trypsin.

As days passed, the search was not completed. The search was considered impractical and terminated in the middle.

In general, for searching for post-translational-modified peptides using the automatic search engine MASCOT, it is recommended to first identify proteins using peptides not treated with post-translational modification and second investigate the possibility of presence/absence of post-translational modification (Journal of Biological Chemistry. 276: 8475-8483, 2001).

Reference Example 2

Under such circumstances, a database consisting of data regarding 888 proteins which were identified above was used for the search, instead of a database comprising information on a huge number of cases (e.g., NCBInr).

The database consisting of data regarding the 888 proteins which were identified above was created as follows. The gi number, which is key information for accessing the NCBInr database was retrieved, and parts defining the protein names and the amino acid sequences were retrieved using a FASTA file of NCBInr used for the search. This was performed for all of the 888 proteins identified above, and thus a database of the FASTA format was newly created. The database created in this manner (hereinafter, referred to as a "database of this experiment") was registered in the MASCOT so as to be searchable. The search conditions were as follows. Oxidation (M), Phospho(ST), and Phospho(Y) were designated as Variable Modification; the number of missed cleavages was set to 2; and the database of this experiment was designated as the database.

Only phosphorylated proteins were searched for, instead of searching for various post-translational modifications at the same time. As a result, 36 peptides obtained a reliability score of 95% or higher. The MS/MS mass spectrum of each of these peptides was checked. As a result, one spectrum was considered to be MS/MS of a phosphorylated peptide. In other words, although the search was performed with limited conditions (the database of this experiment was used), the peptides provided as having a high reliability score were mostly pseudopositive.

As can be appreciated from this, an attempt to comprehensively identify phosphorylated proteins using a search engine (e.g., MASCOT) has a high possibility of resulting in wrong identification. In this experiment, the measurement was performed as many as 1150 times using 11 separation methods of different combinations. Therefore, it was expected that phosphorylated peptides would be separated and detected at a high probability. However, in actuality, it was very difficult to detect phosphorylated peptides from mixed samples for the following reasons. Even among the peptides having the same sequence, phosphorylated peptides have lower detection sensitivity; and in the same peptides in a biological body, only a part of the peptide molecules are phosphorylated. For these reasons, it is considered that phosphorylated peptides cannot be easily detected in a mixed sample, which also contains many other types of peptides.

Reference Example 3

Next, purification of phosphorylated peptides was attempted.

0.1 mL of PHOS-SELECT (produced by Sigma) gel as one type of IMAC column was put into an Eppendorf tube, and mixed with 0.1% acetic acid for 30 seconds. The resultant substance was centrifuged, and the supernatant was discarded. This washing operation was repeated three times. Then, the PSD fraction obtained in reference example 1 was fractionated with a MonoQ column (produced by Amersham). Each fraction was digested with trypsin, and each resultant sample was mixed with acetic acid to be pH 3. Next, the resultant sample was added to PHOS-SELECT and slowly mixed at room temperature for 3 hours. Then, the supernatant was discarded after centrifugation, and the resultant substance was washed three times with 0.5 mL of 0.1% acetic acid. 0.5 mL of 0.15 M ammonia water containing 15% acetonitrile was added thereto, and the resultant substance was centrifuged. Then, the supernatant was collected, and the solvent was evaporated. In this manner, phosphorylated peptides were separated from in the PSD fraction. The obtained residue was dissolved in 20 µl of solvent containing 5% (v/v) acetonitrile and 0.1% TFA, and measured with LC/MS/MS.

Next, phosphomodified proteins were searched for in the obtained measurement data, using the automatic search engine MASCOT and the NCBInr database.

Practically, the protein data of a device NCBInr was saved in a PC server (Windows 2000 Server) of ProLiant ML530 (Compaq; hard disc capacity: 425 GB; memory capacity: 3.767828 GB; CPU: Intel™ XEON™ 2.40 GHz; number of logical CPUs: 4). All the LC/MS/MS data obtained by the measurement described above was also saved in this PC server. The phosphorylated peptides were searched for, using the automatic search engine MASCOT installed in the PC server. The search conditions were as follows. Phospho(ST) and Phospho(Y) were designated as Variable Modification; the number of missed cleavages was set to 2; and NCBInr was designated as the database.

Although only phosphorylation was designated as the post-translational modification, it took 2 hours to retrieve one piece of LC/MS/MS data. 43 phosphorylated peptides were identified at a reliability score of 95% or higher. The mass spectrum of each of these peptides was checked. As a result, the identification result was considered to be highly reliable for 23 identified phosphorylated peptides.

Example 1

Next, the measurement data obtained by separating the phosphorylated peptides in the PSD fraction using an IMAC column and measuring the phosphorylated peptides with LC/MS/MS (reference example 3) was used to search for phosphomodified proteins using the automatic search engine MASCOT (produced by Matrix Science) and the database of this experiment.

Practically, the database of this experiment (reference example 2) was saved in a PC server (Windows 2000 Server) of ProLiant ML530 (Compaq; hard disc capacity: 425 GB; memory capacity: 3.767828 GB; CPU: Intel™ XEON™ 2.40 GHz; number of logical CPUs: 4). All the LC/MS/MS data obtained by the analysis described above (reference example 3) was also saved in this PC server. The search was performed using the automatic search engine MASCOT installed in the PC server. The search conditions were as follows. Phospho (ST) and Phospho(Y) were designated as Variable Modification; the number of missed cleavages was set to 2; and the database of this experiment was designated as the database.

It took only about 3 to 5 minutes to retrieve each piece of LC/MS data. 155 phosphorylated peptides were identified at a reliability score of 95% or higher. The mass spectrum of each of these peptides was checked. As a result, the identification result was considered to be highly reliable for 107 identified phosphorylated peptides.

As described above, by creating a database consisting of data regarding a plurality of proteins in a phosphorylated protein detection target sample, measuring phosphorylated proteins separated from the sample with a mass spectrometer, and analyzing data obtained as a result of the measurement using the created database, plural types of phosphorylated proteins in the sample can be detected with high precision in a short time period. Types of phosphorylated proteins, which are not detectable by the conventional method, can now be detected.

Example 2

(1) Preparation of a Sample Solution 1 mg of ovoalbumin (Sigmna, Cat No. A2512) was dissolved in 1 mL of 0.5 M Tris buffer solution (pH 8.6 at room temperature) containing 8M urea. 1 mg of dithiothreitol (Nacalai Tesque, Inc., Kyoto, Cat No. 14112-52) was added thereto, and the resultant substance was reduced at 37° C. for 1 hour. Then, 2.5 mg of acrylamide (BioRad, Cat No. 161-010) as added thereto, and the resultant substance was incubated at room temperature for 1 hour and thus was alkylated. Then, 2.5 mg of dithiothreitol was added thereto to deactivate unreacted acrylamide, and the resultant substance was dialysized overnight to 5 L of 50 mM ammonia hydrogen carbonate water, using Slide-A-Lyzer MiniDialysis Unit (Pierce, Cat No. 69572). The resultant sample solution was dried by SpeedVac of Savant, and dissolved in 1 mL of 50 mM ammonia hydrogen carbonate water containing 8 M urea. 50 mM ammonia hydrogen carbonate water was added thereto to make the total amount 8 mL. Next, 50 μg of trypsin (Promega K.K., Cat No. V5280) was added thereto, and the resultant substance was digested at 37° C. overnight. The resultant substance was stored at 4° C. in a refrigerator. The resultant substance was set to be used as a sample solution in this example.

(2) Investigation of the Acid (Immobilized Metal Carrier)

First, the effect of an acid, to be added to the purifying solution which is used for purifying phosphorylated proteins using an immobilized metal carrier, was investigated. As acids to be investigated, four types of acids, i.e., acetic acid, formic acid, trifluoroacetic acid, and hydrochloric acid were selected. For each acid, 0.1% (v/v) solution was prepared. Next, 20 μL of the sample solution was diluted 20 folds with 0.1% (v/v) solution of each acid.

Separately, 50 μL of PHOS-Selec Iron Affinity Gel (Sigma-Aldrich, Cat No. P9740) as an immobilized metal carrier was put into an Eppendorf tube having a volume of 1.6 mL, and was washed with 0.1% (v/v) solution of each acid. The concentration of each acid solution was the same as that for diluting the sample solution. The diluted sample solution was added to the substance obtained by washing and vigorously stirred for 30 seconds. The resultant substance was centrifuged at 20000 g (g: gravitational acceleration) for 1 minute, and the supernatant was discarded. Then, 200 μL of 0.1% (v/v) solution of each acid was added thereto, vigorously stirred for 30 seconds, and centrifuged at 20000 g for 1 minute. The supernatant was discarded. Next, 150 mM ammonia water was added thereto, vigorously stirred for 30 seconds, and centrifuged at 20000 g for 1 minute. The supernatant was collected and dried by SpeedVac of Savant.

Next, 5 μL of 33% (v/v) acetonitrile containing 0.1% (v/v) trifluoroacetic acid was added to the dried sample to re-dissolve the sample. 0.5 μL of the re-dissolved sample solution was put on a Matrix Assisted Laser Desorption/Ionization (MALDI) plate. 0.5 μL of matrix solution (alpha-cyano-4-hydroxycinnamic acid, Aldrich, Cat No. 47687-0) saturated with 33% (v/v) acetonitrile containing 0.1% (v/v) trifluoroacetic acid was layered on the sample solution on the MALDI plate, such that the liquid drops would not spread on the sample solution, and was left to naturally dry. The resultant substance was treated with MALDI-TOF/MS measurement by a mass spectrometer (MS) ABI4700 of Applied BioSystems in a linear mode for cation detection.

As a result, it was found that when trifluoroacetic acid or hydrochloric acid was used as the acid, non-specific adsorption to the column was less than when acetic acid or formic acid was used.

(3) Investigation of the Acetonitrile Concentration (Immobilized Metal Carrier)

Next, the acetonitrile concentration in the purifying solution which is used for purifying phosphorylated proteins using an immobilized metal carrier was investigated. The solution, of which the acetonitrile concentration was varied in units of 5% from 0% to 90% (v/v) for the investigation was prepared. The investigation was performed in the same manner as above with 0.1% (v/v) trifluoroacetic acid being added to the purifying solution.

Practically, 20 μL of the sample solution was diluted 20 folds with each concentration of acetonitrile solution. Separately, 50 μL of PHOS-Selec Iron Affinity Gel (Sigma-Aldrich, Cat No. P9740) as an immobilized metal carrier was put into an Eppendorf tube having a volume of 1.6 mL, and washed with an acetonitrile solvent of the same concentrations as that of the solvent used for diluting the sample solution, containing 0.1% (v/v; the same hereinafter) trifluoroacetic acid. The diluted sample solution was added to the substance obtained by washing and vigorously stirred for 30 seconds. The resultant substance was centrifuged at 20000 g for 1 minute, and the supernatant was discarded. Then, 200 μL of acetonitrile solvent of the same concentrations (containing 0.1% trifluoroacetic acid) was added thereto, vigorously stirred for 30 seconds, and centrifuged at 20000 g for 1 minute. The supernatant was discarded. Next, 150 mM ammonia water was added thereto, vigorously stirred for 30 seconds, and centrifuged at 20000 g for 1 minute. The supernatant was collected and dried by SpeedVac of Savant.

Next, 5 μL of 33% acetonitrile containing 0.1% trifluoroacetic acid was added to the dried sample to re-dissolve the sample. 0.5 μL of the re-dissolved sample solution was put on a Matrix Assisted Laser Desorption/Ionization (MALDI) plate. 0.5 μL of matrix solution (alpha-cyano-4-hydroxycinnamic acid, Aldrich, Cat No. 47687-0) saturated with 33% acetonitrile containing 0.1% trifluoroacetic acid was layered on the sample solution on the MALDI plate, such that the liquid drops would not spread on the sample solution, and was left to naturally dry. The resultant substance was treated with MALDI-TOF/MS measurement by a mass spectrometer (MS) ABI4700 of Applied BioSystems in a linear mode for cation detection.

As a result, it was found that when the acetonitrile concentration was in the range of 40% to 60%, non-specific adsorption was less.

The investigation was performed in the same manner using methanol, ethanol, and acetone as organic solvents instead of acetonitrile, while the concentration was varied in units of 10% in the range of 20% to 80%. These organic solvents did not provide any conspicuous effect of reducing the non-specific adsorption at any concentration.

(4) Investigation of the Acid Concentration (Immobilized Metal Carrier)

The concentration of the acid, to be added to the purifying solution which is used for purifying phosphorylated proteins using an immobilized metal carrier, was investigated. The acetonitrile concentration was fixed at 50%. Four types of acids, i.e., acetic acid, formic acid, trifluoroacetic acid, and hydrochloric acid were investigated as above. The acids were investigated at concentrations of 0%, 0.01%, 0.03%, 0.1%, 0.3%, 1%, 3% and 10% in an equivalent manner as above.

Practically, 20 µL of the sample solution was diluted 20 folds with an acetonitrile solution containing each concentration of each acid. Separately, 50 µL of PHOS-Selec Iron Affinity Gel (Sigma-Aldrich, Cat No. P9740) as an immobilized metal carrier was put into an Eppendorf tube having a volume of 1.6 mL, and washed with an acetonitrile solution containing each acid of same concentrations as those in the solvent used for diluting the sample solution. The diluted sample solution was added to the substance obtained by washing and vigorously stirred for 30 seconds. The resultant substance was centrifuged at 20000 g for 1 minute, and the supernatant was discarded. Then, 200 µL of acetonitrile solution containing each acid of the same concentrations was added thereto, vigorously stirred for 30 seconds, and centrifuged at 20000 g for 1 minute. The supernatant was discarded. Next, 150 mM ammonia water was added thereto, vigorously stirred for 30 seconds, and centrifuged at 20000 g for 1 minute. The supernatant was collected and dried by SpeedVac of Savant.

Next, 5 µL of 33% acetonitrile containing 0.1% trifluoroacetic acid was added to the dried sample to re-dissolve the sample. 0.5 µL of the re-dissolved sample solution was put on a Matrix Assisted Laser Desorption/Ionization (MALDI) plate. 0.5 µL of matrix solution (alpha-cyano-4-hydroxycinnamic acid, Aldrich, Cat No. 47687-0) saturated with 33% acetonitrile containing 0.1% trifluoroacetic acid was layered on the sample solution on the MALDI plate, such that the liquid drops would not spread on the sample solution, and was left to naturally dry. The resultant substance was treated with MALDI-TOF/MS measurement by a mass spectrometer (MS) ABI4700 of Applied BioSystems in a linear mode for cation detection.

As a result, when the trifluoroacetic acid concentration was 0.1% or greater but 1% or less, and when the hydrochloric acid concentration was 0.03% or greater but 0.3% or less, non-specific adsorption was recognized to be reduced. By contrast, when acetic acid or formic acid was used, non-specific adsorption was not recognized to be reduced.

From the above-described results, it was found that in a method for purifying phosphorylated proteins using an immobilized metal carrier, phosphorylated proteins are efficiently purified by using a solution containing acetonitrile in a range of 40% (v/v) or greater but 60% (v/v) or less.

It was also found that it is preferable to add, as an acid, trifluoroacetic acid in a range of 0.1% or greater but 1.0% or less, or hydrochloric acid in a range of 0.03% or greater but 0.3% or less.

(5) Investigation of the Titania Carrier

Regarding the purifying solution used for purifying phosphorylated proteins using a titania carrier, substantially the same investigation was performed as in the case of an immobilized metal carrier.

As a result, it was found that in the case of a titania carrier also, phosphorylated proteins are efficiently purified by using a solution containing acetonitrile in a range of 40% (v/v) or greater but 60% (v/v) or less.

It was also found that it is preferable to add, as an acid, trifluoroacetic acid in a range of 0.1% or greater but 1.0% or less, or hydrochloric acid in a range of 0.03% or greater but 0.3% or less.

(6) Influence of Sodium Chloride and a Surfactant

Substantially the same investigation was performed using titania having a large load and 50% acetonitrile solution containing 0.3% trifluoroacetic acid.

Practically, 20 µL of the sample solution was diluted 20 folds with 50% acetonitrile solution containing 0.3% trifluoroacetic acid. Separately, 50 µL of titania carrier (produced by GL Sciences) was put into an Eppendorf tube having a volume of 1.6 mL, and washed with 50% acetonitrile solution containing 0.3% trifluoroacetic acid, which is the same as the solvent used for diluting the sample solution. The diluted sample solution was added to the substance obtained by washing and vigorously stirred for 30 seconds. The resultant substance was centrifuged at 20000 g for 1 minute, and the supernatant was discarded. Then, 200 µL of 50% acetonitrile solution also containing 0.3% trifluoroacetic acid was added thereto, vigorously stirred for 30 seconds, and centrifuged at 20000 g for 1 minute. The supernatant was discarded. Next, 150 mM ammonia water was added thereto, vigorously stirred for 30 seconds, and centrifuged at 20000 g for 1 minute. The supernatant was collected and dried by SpeedVac of Savant.

Next, 5 µL of 33% acetonitrile containing 0.1% trifluoroacetic acid was added to the dried sample to re-dissolve the sample. 0.5 µL of the re-dissolved sample solution was put on a Matrix Assisted Laser Desorption/Ionization (MALDI) plate. 0.5 µL of matrix solution (alpha-cyano-4-hydroxycinnamic acid, Aldrich, Cat No. 47687-0) saturated with 33% acetonitrile containing 0.1% trifluoroacetic acid was layered on the sample solution on the MALDI plate, such that the liquid drops would not spread on the sample solution, and was left to naturally dry. The resultant substance was treated with MALDI-TOF/MS measurement by a mass spectrometer (MS) ABI4700 of Applied BioSystems in a linear mode for cation detection.

To the sample solution, 5 M aqueous solution of sodium chloride had been added beforehand to make the final concentrations of 0, 0.05 M, 0.1 M, 0.2 M, 0.5 M, 0.75 M and 1 M respectively.

Sodium chloride did not have any effect on the purification or non-specific adsorption of the phosphorylated proteins.

In order to investigate the effect of a surfactant on the purifying solution used for purifying phosphorylated proteins, each of Triton X100, Nonidet p40, 5-cyclohexyl-pentyl-beta-D-maltoside, beta-octyl glucoside, and CHAPS was added to the sample solution so that the concentration of the solution was 0.1%, and the effect was examined.

As a result, the three types of surfactants of Triton X100, Nonidet p40, and CHAPS were recognized to have adverse effect on the mass spectrum (could not be removed in the middle), whereas no such problem occurred for 5-cyclohexyl-pentyl-beta-D-maltoside or beta-octyl glucoside.

From these results, it was found that even when about 0.1% 5-cyclohexyl-pentyl-beta-D-maltoside or beta-octyl glucoside or up to 1 M sodium chloride is mixed in the sample solution, there is no specific influence on the method according to the present invention.

(7) Investigation of the Elution Conditions

Regarding the conditions for eluting phosphorylated proteins adsorbing to an immobilized metal carrier or a titania carrier, 150 mM ammonia water, phosphoric acid, sodium dihydrogen phosphate, disodiun hydrogen phosphate were compared. The results were not much different among the substances, and it was found that there is no specific limitation on the conditions for elution.

(8) Comparison with the Conventional Method

Next, a comparative experiment was performed in accordance with the protocol recommended by Sigma. First, the sample solution was diluted 20 folds with 0.1 M acetic acid water. Next, 50 µL of PHOS-Selec Iron Affinity Gel as an immobilized metal carrier was put into an Eppendorf tube having a volume of 1.6 mL, and washed with 0.1 M acetic acid water. The sample solution diluted with 0.1 M acetic acid water was added to the substance obtained by washing and vigorously stirred for 30 seconds. The resultant substance was centrifuged at 20000 g for 1 minute, and the supernatant was discarded. Then, 200 µL of 0.1M acetic acid water was added thereto, vigorously stirred for 30 seconds, and centrifuged at 20000 g for 1 minute. The supernatant was discarded. Next, 150 mM ammonia water was added thereto, vigorously stirred for 30 seconds, and centrifuged at 20000 g for 1 minute. The supernatant was collected and dried by SpeedVac of Savant.

Next, 5 µL of 33% acetonitrile containing 0.1% trifluoroacetic acid was added to the dried sample to re-dissolve the sample. 0.5 µL of the re-dissolved sample solution was put on a Matrix Assisted Laser Desorption/Ionization (MALDI) plate. 0.5 µL of matrix solution (alpha-cyano-4-hydroxycinnamic acid, Aldrich, Cat No. 47687-0) saturated with 33% acetonitrile containing 0.1% trifluoroacetic acid was layered on the sample solution on the MALDI plate, such that the liquid drops would not spread on the sample solution, and was left to naturally dry. The resultant substance was treated with MALDI-TOF/MS measurement by a mass spectrometer (MS) ABI4700 of Applied BioSystems in a linear mode for cation detection.

Figure 3:
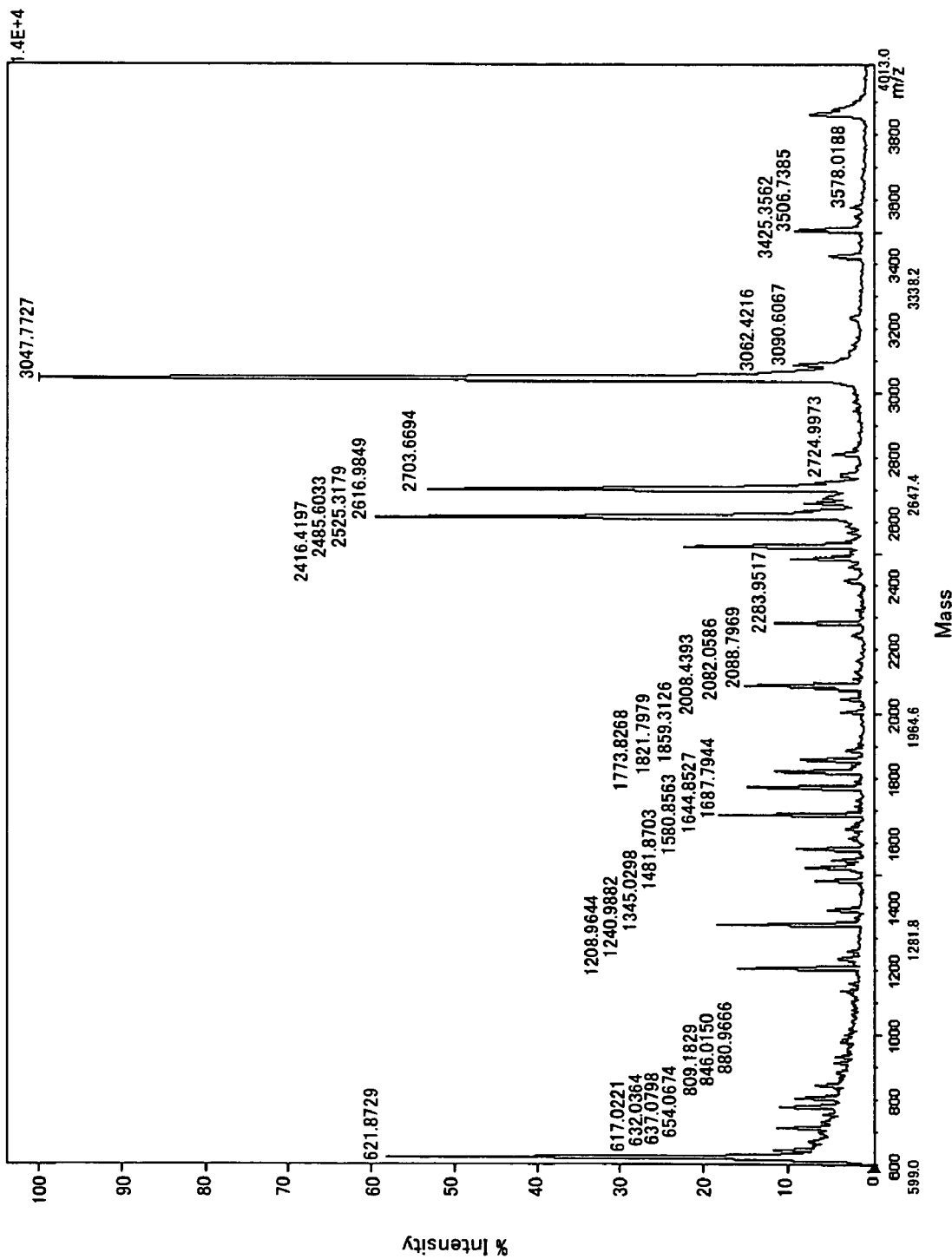
FIG. 3 shows the result of measuring phosphorylated proteins purified by a method for purifying phosphorylated proteins using an immobilized metal carrier. The measurement was performed with a mass spectrometer using 0.1 M acetic acid water. Many proteins in addition to phosphorylated proteins at two sites of ovoalbumin (EVVGSAEAGVDAASVSEEFR 2089 (SEQ ID NO: 1) and LPGFGDSIEAQCGTSVNVH 2082 (SEQ ID NO: 2); the latter was obtained as a result of non-specific cleavage with trypsin, and should be LPGFGDSIEAQCGTSVNVHSSLR (SEQ ID NO: 3)) were detected. As a result, it was not possible to selectively purify the phosphorylated proteins.
Figure 4:
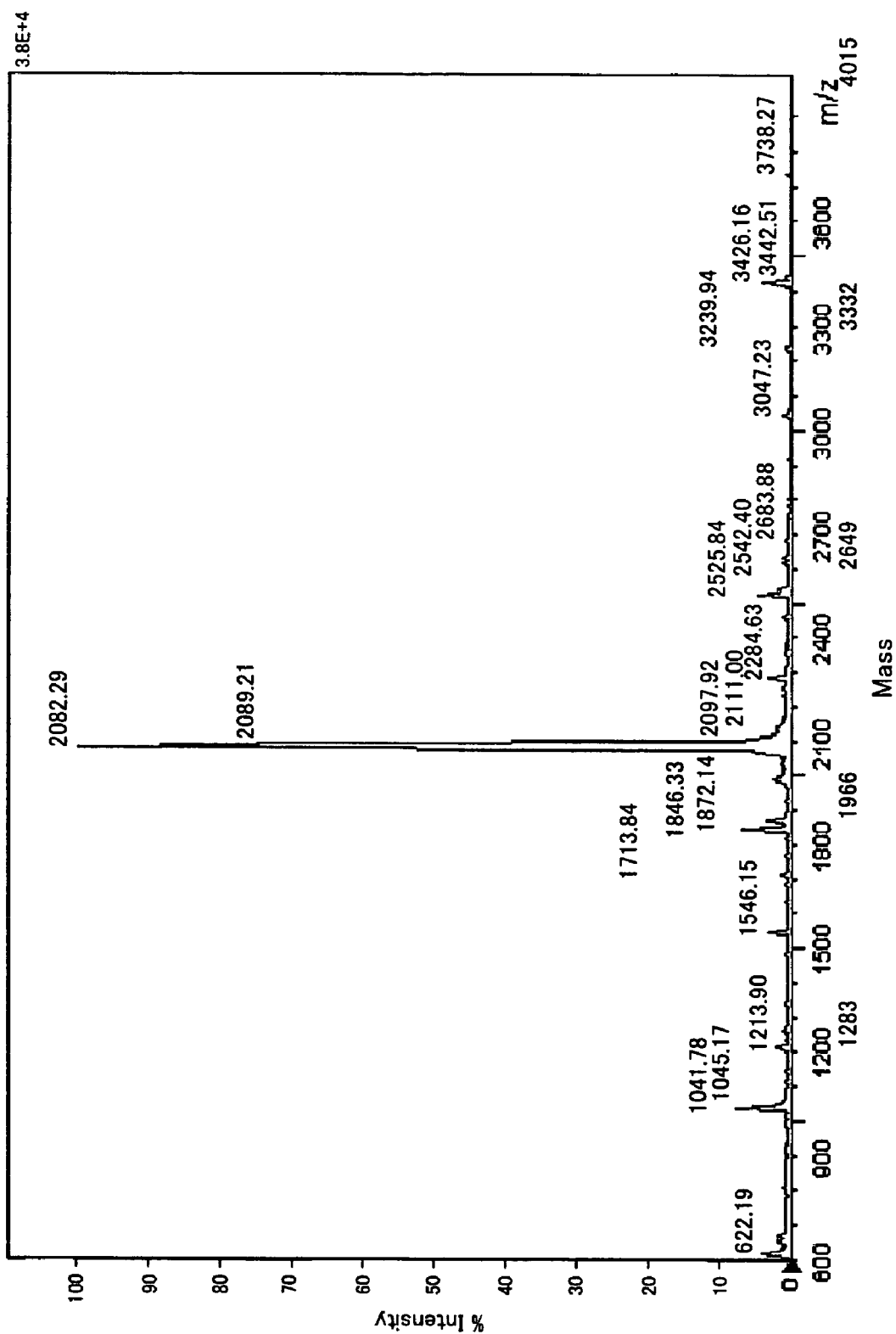
FIG. 4 shows the result of measuring phosphorylated proteins purified by a method for purifying phosphorylated proteins using an immobilized metal carrier. The measurement was performed with a mass spectrometer using 50% acetonitrile solution containing 0.3% trifluoroacetic acid. It is made possible to selectively purify the phosphorylated proteins at two sites of ovoalbumin (EVVGSAEAGVDAASVSEEFR 2089 (SEQ ID NO: 1) and LPGFGDSIEAQCGTSVNVH 2082 (SEQ ID NO: 2); the latter was obtained as a result of non-specific cleavage with trypsin, and should be LPGFGDSIEAQCGTSVNVHSSLR (SEQ ID NO: 3)).

As a result, with the conventional method using 0.1 M acetic acid water, many proteins in addition to phosphorylated proteins at two sites of ovoalbumin (EVVGSAE-AGVDAASVSEEFR 2089 (SEQ ID NO: 1) and LPGFGDS-IEAQCGTSVNVH 2082 (SEQ ID NO: 2); the latter was obtained as a result of non-specific cleavage with trypsin, and should be LPGFGDSIEAQCGTSVNVHSSLR (SEQ ID NO: 3)) were detected. It was not possible to selectively purify the phosphorylated proteins (FIG. 3). By contrast, with the method according to the present invention using 50% acetonitrile solution containing 0.3% trifluoroacetic acid, it is made possible to selectively purify the phosphorylated proteins at two sites of ovoalbumin (EVVGSAEAGVDAASV-SEEFR 2089 (SEQ ID NO: 1) and LPGFGDSIEAQCGTS-VNVH 2082 (SEQ ID NO: 2); the latter was obtained as a result of non-specific cleavage with trypsin, and should be LPGFGDSIEAQCGTSVNVHSSLR (SEQ ID NO: 3)) (FIG. 4).

Industrial Applicability

According to the present invention, plural types of phosphorylated proteins in a sample (e.g., tissue, biological fluid, cell, cellular organ, or protein composite) can be detected with high precision, and the search time can be shortened.

According to the conventional method using an automatic search engine (e.g., MASCOT) and a protein database (e.g., NCBInr, IPI, or Sport), a great number of pseudopositive and pseudonegative results are provided and the search requires a huge amount of time. By creating a database consisting of data regarding plural types of proteins in a phosphorylated protein detection target sample, measuring phosphorylated proteins separated from the sample with a mass spectrometer, and analyzing data obtained as a result of the measurement using the created database, plural types of phosphorylated proteins in the sample can be detected with high precision in a short time period. Types of phosphorylated proteins, which are not detectable by the conventional method, can now be detected.

In addition, according to the present invention, when purifying phosphorylated proteins with an immobilized metal carrier or a titania carrier, a solution containing acetonitrile in a range of 40% (v/v) or greater but 60% (v/v) or less, and preferably also containing trifluoroacetic acid (e.g., in a range of 0.1% (v/v) or greater but 1.0% (v/v) or less) or hydrochloric acid (e.g., in a range of 0.03% (v/v) or greater but 0.3% (v/v) or less) is used. By using such a solution, the non-specific adsorption is drastically decreased and thus one or plural types of phosphorylated proteins in the sample (e.g., tissue, biological fluid, cell, cellular organ, or protein composite) can be efficiently purified.

With the conventional method, proteins having acidic amino acids are more or less bound to an IMAC column because carboxylic acids have affinity to the IMAC column. Therefore, it is not easy to purify only the phosphorylated proteins using the IMAC column. In addition, hydrophobic peptides, which have a non-specific action on IMAC, often cannot be removed. The method according to the present invention can suppress the adsorption of the carboxylic acids or hydrophobic substances to the IMAC column, and thus makes it possible to efficiently purify one or plural types of phosphorylated proteins in a sample (e.g., tissue, biological fluid, cell, cellular organ, or protein composite).

In addition, the problem of the purification method of methylesterifying carboxylic acids of proteins so as to suppress the adsorption of acidic amino acids to the IMAC column is now solved. Namely, the problem that specific purification is often impossible because the esterification does not quantitatively proceed, side reactions occur, the selectivity is not improved as expected, or the peptides are insolubilized after the esterification, is now solved. It has become possible to efficiently purify one or plural types of phosphorylated proteins in a sample (e.g., tissue, biological fluid, cell, cellular organ, or protein composite).

Sequence Listing Free Text

SEQ ID NO 1: Phosphorylated proteins

SEQ ID NO 2: Phosphorylated proteins

SEQ ID NO 3: Phosphorylated proteins

The invention claimed is:

1. A method for detecting plural types of phosphorylated proteins contained in a phosphorylated protein detection target sample comprising the steps of:
   (a) analyzing masses of plural types of proteins contained in a sample which is the same type of sample as said phosphorylated protein detection target sample;
   (b) identifying proteins by referring the mass data obtained from the analysis in step (a) to an existing 1st protein database;
   (c) newly creating a 2nd database which only contains the data of the proteins identified in step (b) and key information and protein names used for search in addition to amino acid sequence information of the proteins identified in step (b);
   (d) separating plural types of phosphorylated proteins from the phosphorylated protein detection target sample;
   (e) analyzing masses of the phosphorylated proteins separated in step (d); and
   (f) retrieving the mass data obtained in step (e) from the 2nd database created in step (c), thereby detecting the phosphorylated proteins.

2. The method according to claim 1, wherein the phosphorylated protein detection target sample is a tissue, a biological fluid, a cell, a cellular organ, or a protein composite.

3. The method according to claim 1 or 2, wherein the step of separating plural types of phosphorylated proteins from the phosphorylated protein detection target sample uses an immobilized metal carrier or a titania carrier and a solution containing acetonitrile in a range of 40% (v/v) or greater but 60% (v/v) or less.

* * * * *

SEQUENCE LISTING

<160> NUMBER OF SEQ ID NOS: 5

<210> SEQ ID NO 1
<211> LENGTH: 20
<212> TYPE: PRT
<213> ORGANISM: Artificial
<220> FEATURE:
<223> OTHER INFORMATION: phosphorylated protein

<400> SEQUENCE: 1

Glu Val Val Gly Ser Ala Glu Ala Gly Val Asp Ala Ala Ser Val Ser
1               5                   10                  15

Glu Glu Phe Arg
            20

<210> SEQ ID NO 2
<211> LENGTH: 19
<212> TYPE: PRT
<213> ORGANISM: Artificial
<220> FEATURE:
<223> OTHER INFORMATION: phosphorylated protein

<400> SEQUENCE: 2

Leu Pro Gly Phe Gly Asp Ser Ile Glu Ala Gln Cys Gly Thr Ser Val
1               5                   10                  15

Asn Val His

<210> SEQ ID NO 3
<211> LENGTH: 23
<212> TYPE: PRT
<213> ORGANISM: Artificial
<220> FEATURE:
<223> OTHER INFORMATION: phosphorylated protein

<400> SEQUENCE: 3

Leu Pro Gly Phe Gly Asp Ser Ile Glu Ala Gln Cys Gly Thr Ser Val
1               5                   10                  15

Asn Val His Ser Ser Leu Arg
            20

<210> SEQ ID NO 4
<211> LENGTH: 24
<212> TYPE: PRT
<213> ORGANISM: Homo sapiens

<400> SEQUENCE: 4

Glu Arg Asp Glu Gly Ser Tyr Tyr Cys Ala Cys Asp Thr Val Leu Gly
1               5                   10                  15

Asp Thr Pro Ser Ser Trp Asp Thr
            20

<210> SEQ ID NO 5
<211> LENGTH: 501
<212> TYPE: PRT
<213> ORGANISM: Homo sapiens

<400> SEQUENCE: 5

Met Ala Ala Ser Trp Arg Leu Gly Cys Asp Pro Arg Leu Leu Arg Tyr
1               5                   10                  15

Leu Val Gly Phe Pro Gly Arg Arg Ser Val Gly Leu Val Lys Gly Ala
            20                  25                  30

Leu Gly Trp Ser Val Ser Arg Gly Ala Asn Trp Arg Trp Phe His Ser

-continued

```
              35                  40                  45
Thr Gln Trp Leu Arg Gly Asp Pro Ile Lys Ile Leu Met Pro Ser Leu
 50                  55                  60

Ser Pro Thr Met Glu Glu Gly Asn Ile Val Lys Trp Leu Lys Lys Glu
 65                  70                  75                  80

Gly Glu Ala Val Ser Ala Gly Asp Ala Leu Cys Glu Ile Glu Thr Asp
                 85                  90                  95

Lys Ala Val Val Thr Leu Asp Ala Ser Asp Gly Ile Leu Ala Lys
                100                 105                 110

Ile Val Val Glu Glu Gly Ser Lys Asn Ile Arg Leu Gly Ser Leu Ile
                115                 120                 125

Gly Leu Ile Val Glu Glu Gly Glu Asp Trp Lys His Val Glu Ile Pro
130                 135                 140

Lys Asp Val Gly Pro Pro Pro Val Ser Lys Pro Ser Glu Pro Arg
145                 150                 155                 160

Pro Ser Pro Glu Pro Gln Ile Ser Ile Pro Val Lys Lys Glu His Ile
                165                 170                 175

Pro Gly Thr Leu Arg Phe Arg Leu Ser Pro Ala Ala Arg Asn Ile Leu
                180                 185                 190

Glu Lys His Ser Leu Asp Ala Ser Gln Gly Thr Ala Thr Gly Pro Arg
                195                 200                 205

Gly Ile Phe Thr Lys Glu Asp Ala Leu Lys Leu Val Gln Leu Lys Gln
                210                 215                 220

Thr Gly Lys Ile Thr Glu Ser Arg Pro Thr Pro Ala Pro Thr Ala Thr
225                 230                 235                 240

Pro Thr Ala Pro Ser Pro Leu Gln Ala Thr Ser Gly Pro Ser Tyr Pro
                245                 250                 255

Arg Pro Val Ile Pro Pro Val Ser Thr Pro Gly Gln Pro Asn Ala Val
                260                 265                 270

Gly Thr Phe Thr Glu Ile Pro Ala Ser Asn Ile Arg Arg Val Ile Ala
                275                 280                 285

Lys Arg Leu Thr Glu Ser Lys Ser Thr Val Pro His Ala Tyr Ala Thr
290                 295                 300

Ala Asp Cys Asp Leu Gly Ala Val Leu Lys Val Arg Gln Asp Leu Val
305                 310                 315                 320

Lys Asp Asp Ile Lys Val Ser Val Asn Asp Phe Ile Ile Lys Ala Ala
                325                 330                 335

Ala Val Thr Leu Lys Gln Met Pro Asp Val Asn Val Ser Trp Asp Gly
                340                 345                 350

Glu Gly Pro Lys Gln Leu Pro Phe Ile Asp Ile Ser Val Ala Val Ala
                355                 360                 365

Thr Asp Lys Gly Leu Leu Thr Pro Ile Ile Lys Asp Ala Ala Ala Lys
                370                 375                 380

Gly Ile Gln Glu Ile Ala Asp Ser Val Lys Ala Leu Ser Lys Lys Ala
385                 390                 395                 400

Arg Asp Gly Lys Leu Leu Pro Glu Glu Tyr Gln Gly Gly Ser Phe Ser
                405                 410                 415

Ile Ser Asn Leu Gly Met Phe Gly Ile Asp Glu Phe Thr Ala Val Ile
                420                 425                 430

Asn Pro Pro Gln Ala Cys Ile Leu Ala Val Gly Arg Phe Arg Pro Val
                435                 440                 445

Leu Lys Leu Thr Glu Asp Glu Glu Gly Asn Ala Lys Leu Gln Gln Arg
450                 455                 460
```

-continued

```
Gln Leu Ile Thr Val Thr Met Ser Ser Asp Ser Arg Val Val Asp Asp
465                 470                 475                 480

Glu Leu Ala Thr Arg Phe Leu Lys Ser Phe Lys Ala Asn Leu Glu Asn
                485                 490                 495

Pro Ile Arg Leu Ala
                500
```